(12) United States Patent
Gryaznov et al.

(10) Patent No.: US 9,572,891 B2
(45) Date of Patent: *Feb. 21, 2017

(54) OLIGONUCLEOTIDE CONJUGATES

(71) Applicant: Geron Corporation, Menlo Park, CA (US)

(72) Inventors: Sergei M. Gryaznov, San Mateo, CA (US); Krisztina Pongracz, Oakland, CA (US); Richard L. Tolman, Incline Village, NV (US); Gregg B. Morin, Vancouver (CA)

(73) Assignee: Geron Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,572

(22) Filed: Jun. 2, 2015

(65) Prior Publication Data

US 2015/0374841 A1 Dec. 31, 2015

Related U.S. Application Data

(60) Continuation of application No. 13/892,065, filed on May 10, 2013, now Pat. No. 9,072,790, which is a continuation of application No. 12/504,931, filed on Jul. 17, 2009, now Pat. No. 8,440,635, which is a division of application No. 10/255,535, filed on Sep. 25, 2002, now Pat. No. 7,563,618, which is a continuation-in-part of application No. PCT/US02/09138, filed on Mar. 21, 2002.

(60) Provisional application No. 60/278,322, filed on Mar. 23, 2001.

(51) Int. Cl.
C07H 21/00 (2006.01)
A61K 31/7088 (2006.01)
A61K 47/48 (2006.01)

(52) U.S. Cl.
CPC ......... *A61K 47/48092* (2013.01); *C07H 21/00* (2013.01)

(58) Field of Classification Search
USPC ......... 435/6.12, 6.14, 91.1, 184, 375; 514/1, 514/19.3, 44; 536/23.1, 22.1, 25.32, 24.5, 23.2, 536/23.32
See application file for complete search history.

(56) References Cited

U.S. PATENT DOCUMENTS

| | | |
|---|---|---|
| 4,965,349 A | 10/1990 | Woo et al. |
| 5,583,016 A | 12/1996 | Villeponteau et al. |
| 5,591,607 A | 1/1997 | Gryaznov et al. |
| 5,599,922 A | 2/1997 | Gryaznov et al. |
| 5,616,298 A | 4/1997 | Mattingly |
| 5,643,890 A | 7/1997 | Iversen et al. |
| 5,656,638 A | 8/1997 | Gaeta et al. |
| 5,695,932 A | 12/1997 | West et al. |
| 5,726,297 A | 3/1998 | Gryaznov et al. |
| 5,776,694 A | 7/1998 | Sheiness et al. |
| 5,814,447 A | 9/1998 | Ishiguru et al. |
| 5,824,793 A | 10/1998 | Hirschbein et al. |
| 5,837,857 A | 11/1998 | Villeponteau et al. |
| 5,863,936 A | 1/1999 | Gaeta et al. |
| 5,891,639 A | 4/1999 | Harley et al. |
| 5,952,490 A | 9/1999 | Hanecak et al. |
| 5,958,680 A | 9/1999 | Villeponteau et al. |
| 6,004,939 A | 12/1999 | Chen et al. |
| 6,015,710 A | 1/2000 | Shay et al. |
| 6,040,138 A | 3/2000 | Lockhart et al. |
| 6,046,307 A | 4/2000 | Shay et al. |
| 6,261,836 B1 | 7/2001 | Cech et al. |
| 6,294,650 B1 | 9/2001 | Shay et al. |
| 6,506,559 B1 | 1/2003 | Fire et al. |
| 6,608,036 B1 | 8/2003 | Gryaznov et al. |
| 7,067,497 B2 | 6/2006 | Hanecak et al. |
| 7,563,618 B2 * | 7/2009 | Gryaznov ........ A61K 47/48092 435/375 |
| 9,072,790 B2 * | 7/2015 | Gryaznov |
| 2001/0039263 A1 | 11/2001 | Matthes et al. |
| 2004/0034023 A1 | 2/2004 | Mergny et al. |
| 2005/0070575 A1 | 3/2005 | Mailiet et al. |
| 2005/0233455 A1 | 10/2005 | Damha et al. |
| 2007/0270363 A1 | 11/2007 | Bennett et al. |

FOREIGN PATENT DOCUMENTS

| | | |
|---|---|---|
| CA | 2382521 | 3/2001 |
| DE | 19720151 | 11/1998 |
| EP | 0490281 | 6/1992 |
| JP | 2001-013147 | 1/2001 |
| JP | 2001-524100 | 11/2001 |
| JP | 2002-523335 | 7/2002 |
| JP | 2005-508634 | 4/2005 |
| JP | 7-505627 | 7/2005 |

(Continued)

OTHER PUBLICATIONS

Agrawal, S. , "Antisense oligonucleotides: towards clinical trials", TIBTECH 14(10), 1996, 376-87.

Agrawal, Sudhir et al., "Antisense therapeutics: is it as simple as complementary base recognition?", Molecular Med. Today, vol. 6, pp. 72-81 (2000), 2000, 72-81.

Asseline, U. et al., "Nucleic acid-binding molecules with high affinity and base sequence specificity: Intercalating agents covalently linked to oligodeoxynucleotides", Proc. Natl. Acad. Sci. USA 81, (1984), pp. 3297-3301.

Augustyns, K. et al., "Influence of the incorporation of (S)-9-(3,4-dihydroxy-butyl)adenine on the enzymatic stability and base-pairing properties of oligodeoxynucleotides", Nucl. Acids Res. 19(10), 1991, 2587-93.

(Continued)

*Primary Examiner* — Jane Zara
(74) *Attorney, Agent, or Firm* — Glenn Foulds; Carol L. Francis; Bozicevic, Field & Francis LLP

(57) ABSTRACT

Oligonucleotide conjugates, where an oligonucleotide is covalently attached to an aromatic system, are provided. In particular embodiments the oligonucleotide is complementary to the RNA component of human telomerase and is covalently attached to a nucleobase via an optional linker. The conjugates inhibit telomerase enzyme activity.

4 Claims, 3 Drawing Sheets

(56) References Cited

FOREIGN PATENT DOCUMENTS

| WO | 93/20060 | 10/1993 |
| --- | --- | --- |
| WO | 94/01550 | 1/1994 |
| WO | 94/08053 | 4/1994 |
| WO | 96/23508 | 8/1996 |
| WO | 97/02279 | 1/1997 |
| WO | 97/37691 | 10/1997 |
| WO | 98/33503 | 8/1998 |
| WO | 98/47911 | 10/1998 |
| WO | 99/50279 | 10/1999 |
| WO | 00/08140 | 2/2000 |
| WO | 01/18015 | 3/2001 |
| WO | 01/96339 | 12/2001 |
| WO | 02/051409 | 7/2002 |
| WO | 02/076397 | 10/2002 |
| WO | 02/077184 | 10/2002 |
| WO | 2004/029277 | 4/2004 |

OTHER PUBLICATIONS

Braasch, D. et al., "Novel antisense and peptide nucleic acid strategies for controlling gene expression", Biochemistry 41(14), 2002, 4503-10.
Branch, A., "A good antisense molecule is hard to find", Trends in Biol. Sci. 23, 1998, 45-50.
Chen, J. et al., "Secondary structure of vertebrate telomerase RNA", Cell 100, 2000, pp. 503-514.
Chen, J. et al., "Synthesis of an Oligonucleotide-Intercalator Conjugate in which the Linker Chain is Attached via the Phenolic Hydroxyl Group of Fagaronine", Tetrahedron Lett. 33 (17), 1992, 2275-8.
Chirila, T. et al., "The use of synthetic polymers for delivery of therapeutic antisense oligodeoxynucleotides", Biomaterials 23, 2002, pp. 321-342.
Crooke, Stanley T., "Progress in Antisense Technology", Ann. rev. Medicine, vol. 55, pp. 61-95 (2004), 2004, 61-95.
Damm, K. et al., "A highly selective telomerase inhibitor limiting human cancer cell proliferation", EMBO J. 20(24), 2001, 6958-68.
Feng, J. et al., "The RNA component of human telomerase", Science 269, 1995, 1236-41.
Gewirtz, A. et al., "Facilitating oligonucleotide delivery: helping antisense deliver on its promise", Proc. Natl. Acad. Sci. USA 93(8), 1996, 3161-3.
Glukhov, A. et al., "Inhibition of telomerase activity of melanoma cells in vitro by antisense oligonucleotides", Biochem. Biophys. Res. Comm. 248, 1998, 368-71.
Gomez, D. et al., "Preferential incorporation of 3'-azido-2',3'-dideoxythymidine (AZT) in telomeric sequences of CHO cells", Intl. J. Oncol. 7, 1995, 1057-60.
Gryaznov, S. et al., "Synthesis and properties of oligonucleotides containing aminodeoxythymidine units", Nucl. Acids Res. 20(13), 1992, 3403-9.
Jang, Jae-Hyung et al., "Gene Delivery from Polymer Scaffolds for Tissue Engineering", Expert Reg. Medical Devices, vol. 1, No. 1, pp. 127-138 (2004), 2004, 127-138.
Kim, M. et al., "A low threshold level of expression of mutant-template telomerase RNA inhibits human tumor cell proliferation", Proc. Natl. Acad. Sci. USA 98(14), 2001, pp. 7982-7987.
Lichtsteiner, S. et al., "Telomerase—A target for anticancer therapy", Ann. NY Acad. Sci. 886, 1999, 1-11.
Matsukura, M., "Research and development of antisense as a method for controlling the in vivo proliferation of HIV and the pathological onset", Basic Study on pathology and control of AIDS in 1995-1997 fiscal years, Y. Nagai, Ed., 1999, 521-5.
Mergny, J. et al., "Telomerase inhibitors based on quadruplex ligands selected by a fluorescence assay", Proc. Natl. Acad. Sci. USA 98(6), (2001), pp. 3062.
Nielsen, P. et al., "Incorporation of (R)- and (S)-3',4'-seco-thymidine into oligodeoxynucleotides: hybridization properties and enzymatic stability", Nucl. Acids Res. 22(5), 1994, 703-10.
Opalinska, Joanna B. et al., "Nucleic-acid therapeutics: basic principles and recent applications", Nature Rev. Drug Discovery 1, 2002, 503-14.
Peracchi, Alessio et al., "Prospects for Antiviral Ribozymes and Deoxyribozymes", Rev. Med. Virol., vol. 14, pp. 47-64 (2004), 2004, 47-64.
Pongracz, K. et al., "Alpha-Oligodeoxyribonucleotide N3'→P5' phosphoramidates: synthesis and duplex formation", Nucl. Acids Res. 26(4), 1998, 1099-106.
Rando, R. et al., "Development of novel nucleoside analogues for use against drug resistant strains of HIV-1", Drug Discovery Today 5(10), 2000, 465-76.
Strahl, C. et al., "The effects of nucleoside analogs on telomerase and telomeres in Tetrahymena", Nucl. Acids Res. 22(6), 1994, 893-900.
Tamm, I. et al., "Antisense therapy in oncology: new hope for an old idea?", The Lancet 358, 2001, 489-97.
Vorobjev, P. et al., "Nuclease resistance and RNase H sensitivity of oligonucleotides bridged by oligomethylenediol and oligoethylene glycol linkers", Antisense & Nucl. Acid Drug Dev. 11, 2001, 77-85.
White, L. et al., "Telomerase inhibitors", Trends Biotechnol. 19(3), 2001, 114-20.
Yegorov, Y. et al., "Blockade of telomerase function by nucleoside analogs", Biochem. (Moscow) 62(11), 1997, 1296-305.

* cited by examiner

SEQUENCE LISTING

```
<160> NUMBER OF SEQ ID NOS: 8

<210> SEQ ID NO 1
<211> LENGTH: 11
<212> TYPE: RNA
<213> ORGANISM: Homo sapiens

<400> SEQUENCE: 1
cuaacccuaa c                                                            11

<210> SEQ ID NO 2
<211> LENGTH: 13
<212> TYPE: DNA
<213> ORGANISM: Artificial Sequence
<220> FEATURE:
<223> OTHER INFORMATION: oligonucleotide conjugate

<400> SEQUENCE: 2
tagggttaga caa                                                          13

<210> SEQ ID NO 3
<211> LENGTH: 11
<212> TYPE: DNA
<213> ORGANISM: Artificial sequence
<220> FEATURE:
<223> OTHER INFORMATION: Oligonucleotide

<400> SEQUENCE: 3
gttagggtta g                                                            11

<210> SEQ ID NO 4
<211> LENGTH: 11
<212> TYPE: DNA
<213> ORGANISM: Artificial sequence
<220> FEATURE:
<223> OTHER INFORMATION: Oligonucleotide

<400> SEQUENCE: 4
gattgggatt g                                                            11

<210> SEQ ID NO 5
<211> LENGTH: 26
<212> TYPE: DNA
<213> ORGANISM: Artificial sequence
<220> FEATURE:
<223> OTHER INFORMATION: oligonucleotide

<400> SEQUENCE: 5
```

```
gtagacctgt taccaguuag gguuag                                              26

<210> SEQ ID NO 6
<211> LENGTH: 26
<212> TYPE: DNA
<213> ORGANISM: Artificial sequence
<220> FEATURE:
<223> OTHER INFORMATION: oligonucleotide

<400> SEQUENCE: 6
ctaaccctaa ctggtaacag gtctac                                             26

<210> SEQ ID NO 7
<211> LENGTH: 18
<212> TYPE: DNA
<213> ORGANISM: Artificial sequence
<220> FEATURE:
<223> OTHER INFORMATION: biotinylated primer

<400> SEQUENCE: 7
aatccgtcga gcagagtt                                                      18

<210> SEQ ID NO 8
<211> LENGTH: 71
<212> TYPE: DNA
<213> ORGANISM: Artificial sequence
<220> FEATURE:
<223> OTHER INFORMATION: 5.4 nM labeled probe
<220> FEATURE:
<221> NAME/KEY: misc_feature
<222> LOCATION: (22)..(22)
<223> OTHER INFORMATION: labeled with 33P
<220> FEATURE:
<221> NAME/KEY: polyA_site
<222> LOCATION: (22)..(71)
<223> OTHER INFORMATION: a can be from 1 to 50 nucleotides

<400> SEQUENCE: 8
ccctaaccct aaccctaacc caaaaaaaaa aaaaaaaaaa aaaaaaaaaa aaaaaaaaaa         60
aaaaaaaaaa a                                                             71
```

OLIGONUCLEOTIDE CONJUGATES

REFERENCE TO RELATED APPLICATIONS

This application is a continuation of U.S. Pat. No. 13/892,065, filed May 10, 2013, which is a continuation of U.S. Pat. No. 12/504,931, filed Jul. 17, 2009, which is a divisional of U.S. Pat. No. 10/255,535, filed Sep. 25, 2002, which is a continuation-in-part of PCT/US02/09138, filed Mar. 21, 2002, designating the U.S. and to be published in English 18 months after the first priority date pursuant to Article 21 (2) of the Patent Cooperation Treaty. This application also claims priority to U.S. provisional patent application 60/278,322, filed Mar. 23, 2001. These priority applications are herein incorporated by reference.

FIELD OF THE INVENTION

The present invention relates to covalent oligonucleotide conjugates. More particularly, the present invention is directed to covalent oligonucleotide conjugates that are designed to inhibit the activity of telomerase, an enzyme that is preferentially expressed in, and required for the growth of, cancer cells.

BACKGROUND OF THE INVENTION

Oligonucleotide Chemistry

Nucleic acid polymer chemistry has played a crucial role in many developing technologies in the pharmaceutical, diagnostic, and analytical fields, and more particularly in the subfields of antisense and antigene therapeutics, combinatorial chemistry, branched DNA signal amplification, and array-based DNA diagnostics and analysis. Much of this chemistry has been directed to improving the binding strength, specificity, and nuclease resistance of natural nucleic acid polymers, such as DNA. Unfortunately, improvements in one property, such as nuclease resistance, often involve trade-offs against other properties, such as binding strength. Examples of such trade-offs abound: peptide nucleic acids (PNAs) display good nuclease resistance and binding strength, but have reduced cellular uptake in test cultures (e.g. Hanvey et al., Science, 258:1481-1485, 1992); phosphorothioates display good nuclease resistance and solubility, but are typically synthesized as P-chiral mixtures and display several sequence-non-specific biological effects (e.g. Stein et al., Science, 261:1004-1012, 1993); methylphosphonates display good nuclease resistance and cellular uptake, but are also typically synthesized as P-chiral mixtures and have reduced duplex stability, and so on.

Recently, a new class of oligonucleotide analog has been developed having so-called N3'→P5' phosphoramidate internucleoside linkages, which display favorable nucleic acid binding properties, nuclease resistance, and water solubility (Gryaznov and Letsinger, Nucleic Acids Research, 20:3403-3409, 1992; Chen et al., Nucleic Acids Research, 23:2661-2668, 1995; Gryaznov et al., Proc. Natl. Acad. Sci., 92:5798-5802, 1995; and Gryaznov et al., J. Am. Chem. Soc., 116:3143-3144, 1994). Uniformly modified phosphoramidate compounds contain a 3'-amino group at each of the 2'-deoxyfuranose nucleoside residues replacing a 3'-oxygen atom. The synthesis and properties of oligonucleotide N3'→P5' phosphoramidates are also described in U.S. Pat. Nos. 5,591,607; 5,599,922; 5,726,297; and 5,824,793.

Oligonucleotides conjugated to a signal generating system have been used as tools in diagnostic applications, such as fluorescent in situ hybridization (FISH). For example, specific microorganism (U.S. Pat. No. 5,776,694) or telomerase-expressing cells (U.S. Pat. No. 5,891,639) were identified by labeling nucleic acids that were complementary to sequences unique to the target organism or the telomerase enzyme, respectively, and then contacting the probe with the target. Once the probe had formed a hybrid with the target, the hybrid was detected by activating the signal generating system that was bound to the probe. In another use, labeled probes were used in DNA microarray experiments (See U.S. Pat. No. 6,040,138). Typically, probes from a biological sample were amplified in the presence of nucleotides that had been coupled to a reporter group, such as a fluorescent label, thereby creating labeled probes. The labeled probes were then incubated with the microarrays so that the probe sequences hybridized to the complementary sequences immobilized on the microarray. A scanner was then used to determine the levels and patterns of fluorescence.

The present invention relates to a new class of oligonucleotide conjugates having telomerase inhibiting activity.

Telomerase

Telomerase is a ribonucleoprotein that catalyzes the addition of telomeric repeat sequences to chromosome ends. See Blackburn, 1992, Annu. Rev. Biochem., 61:113-129. There is an extensive body of literature describing the connection between telomeres, telomerase, cellular senescence and cancer (for a general review, see Oncogene, volume 21, January 2002, which is an issue focused on telomerase). Telomerase has therefore been identified as an excellent target for cancer therapeutic agents (see Lichsteiner et al., Annals New York Acad. Sci. 886:1-11, 1999)

Genes encoding both the protein and RNA components of human telomerase have been cloned and sequenced (See U.S. Pat. Nos. 6,261,836 and 5,583,016, respectively) and much effort has been spent in the search for telomerase inhibitors. Telomerase inhibitors identified to date include small molecule compounds and oligonucleotides. By way of example, WO01/18015 describes the use of oligonucleotides that comprise N3'→P5' thio-phosphoramidate internucleoside linkages, and which are complementary to the sequence of the human telomerase RNA component, to inhibit telomerase activity.

SUMMARY OF THE INVENTION

The compositions and methods of the present invention relate to compounds comprising an oligonucleotide and at least one covalently linked group, preferably an aromatic system. The sequence of the oligonucleotide is selected to be complementary to the RNA component of telomerase, and the covalently linked aromatic system can be, for example, a polyaromatic hydrocarbon, a mono- or poly-cyclic heteroaromatic system, or a nucleobase (including modified nucleobases and nucleobase analogs). The aromatic group is typically, although not necessarily, covalently attached to either the 3'-position or the 5'-position of the oligonucleotide, and in particular embodiments aromatic groups may be attached to each of the 3'- and 5'-positions. In their simplest form, the compounds of the invention can be represented by the formula:

(A-L-)$_n$-O wherein A comprises the aromatic group, L is an optional linker group (i.e., a linker or a direct bond), O is an oligonucleotide and n is an integer between 1 and 1+m where m is the total number of nucleosides comprising the oligonucleotide. In this formula, the bond—is used in the conventional manner to indicate a covalent linkage between moieties at each end of the bond. In preferred embodiments, n=1 or 2 and the A moiety is attached to the oligonucleotide component at one or each of the 3'- and 5'-terminii.

The oligonucleotide components of the compounds typically comprise 2-50 nucleosides (i.e., m =2-50), and the intersubunit linkages between the nucleosides can be formed using any compatible chemistry, including, but not limited to: phosphodiester; phosphotriester, methylphosphonate; P3'→N5' phosphoramidate; N3'→P5' phosphoramidate; N3'→P5' thio-phosphoramidate; and phosphorothioate linkages. In preferred embodiments, the sequence of the oligonucleotide O is selected such that it is complementary to the template region of the RNA component of telomerase.

In particular embodiments, the covalently linked aromatic moiety A is a pyrimidine or purine nucleobase or an analog or derivative thereof. Particular examples include guanine, cytosine, thymine, uracil and adenine. In other embodiments, the covalently linked aromatic moiety A is polyaromatic substituted or unsubstituted hydrocarbon such as an intercalator, reporter molecule, chromophore or fluorophore. Particular examples include trityl-based groups, fluoresceins, rhodamines, coumarins, acridines, and anthraquinones. One or more A moieties may be attached to the oligonucleotide at the 3'- or 5'-terminus or at an intermediate location on the oligonucleotide. The A moiety may be attached (with or without a linker) to any compatible group on the oligonucleotide, including to the sugar ring, the internucleoside linkage, and the base. In conjugates having more than one A moiety attached to the oligonucleotide, each A moiety, each linker, and each site of attachment may be independently chosen. In certain embodiments involving conjugates having more than one A moiety, a first A moiety is covalently linked to the oligonucleotide O, and other A groups are covalently linked to the first A moiety, optionally through a linker group.

A variety of linkers (L) may be used to covalently link the A moiety to the oligonucleotide O, or sequentially join A moieties, as described herein. Where A is selected to be a nucleobase, it is preferred that the linker L be a relatively flexible linker so as to permit movement of the A moiety relative to the oligonucleotide O or to sequentially joined other A moieties. Where no linker is required, L is a direct bond between A and O.

The oligonucleotide conjugate compounds of the present invention may be used in methods to inhibit telomerase enzymatic activity. Such methods comprise contacting a telomerase enzyme with a compound of the invention. The oligonucleotide conjugate compounds of the present invention may also be used to inhibit telomerase in cells that express telomerase, thereby inhibiting the proliferation of such cells. Such methods comprise contacting a cell or cells having telomerase activity with a compound of the invention. Cells treated in this manner, which may be cells in vitro, or cells in vivo, will undergo telomere shortening and cease proliferating. Since cancer cells require telomerase activity to proliferate, the compounds of the invention are particularly useful for inhibiting the growth of cancer cells, and may be used in therapeutic applications to treat cancer.

Aspects of the invention therefore include oligonucleotide conjugate compounds as described herein for use in medicine, and in particular for use in treating cancer.

Also provided herein are pharmaceutical compositions comprising an oligonucleotide conjugate according to the invention formulated in a pharmaceutically acceptable excipient.

Two oligonucleotide conjugates that are illustrative of the compounds of the present invention are shown schematically below, with the three components A, L and O shown as bracketed. In Illustration A, the two 3'-nucleosides of the oligonucleotide (O) are shown, and the aromatic group (A) fluorescein is linked to the 3'-end of the oligonucleotide through a linker (L, a thiourea group) attached to the sugar ring of the 3' terminal nucleoside. In Illustration B, the two 3'-nucleosides of the oligonucleotide (O) are shown, and the aromatic group (A) guanine is linked to the 3'-end of the oligonucleotide through a linker (L, an open sugar ring) attached to the thiophosphoramidate internucleoside linkage of the 3' terminal nucleoside. In each illustration, B represents the nucleoside bases of the oligonucleotide, and the oligonucleoside backbone linkages shown are N3'→P5' thio-phosphoramidate linkages.

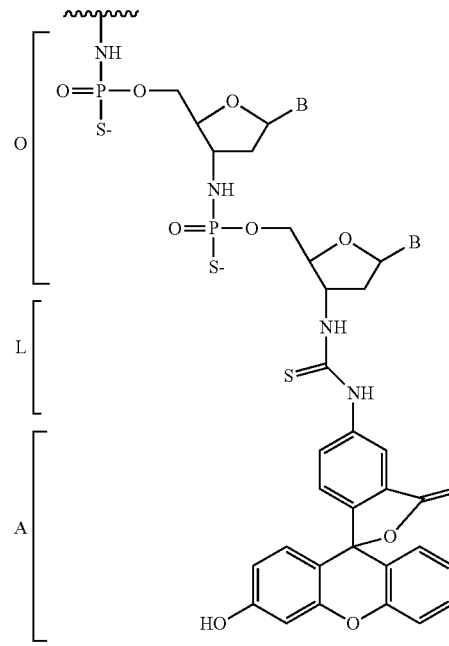

Illustration A

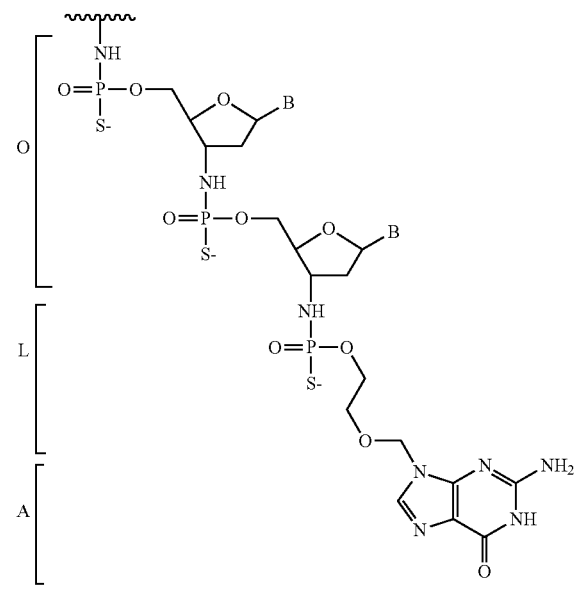

Illustration B

DETAILED DESCRIPTION

A. Definitions

Figure 1:
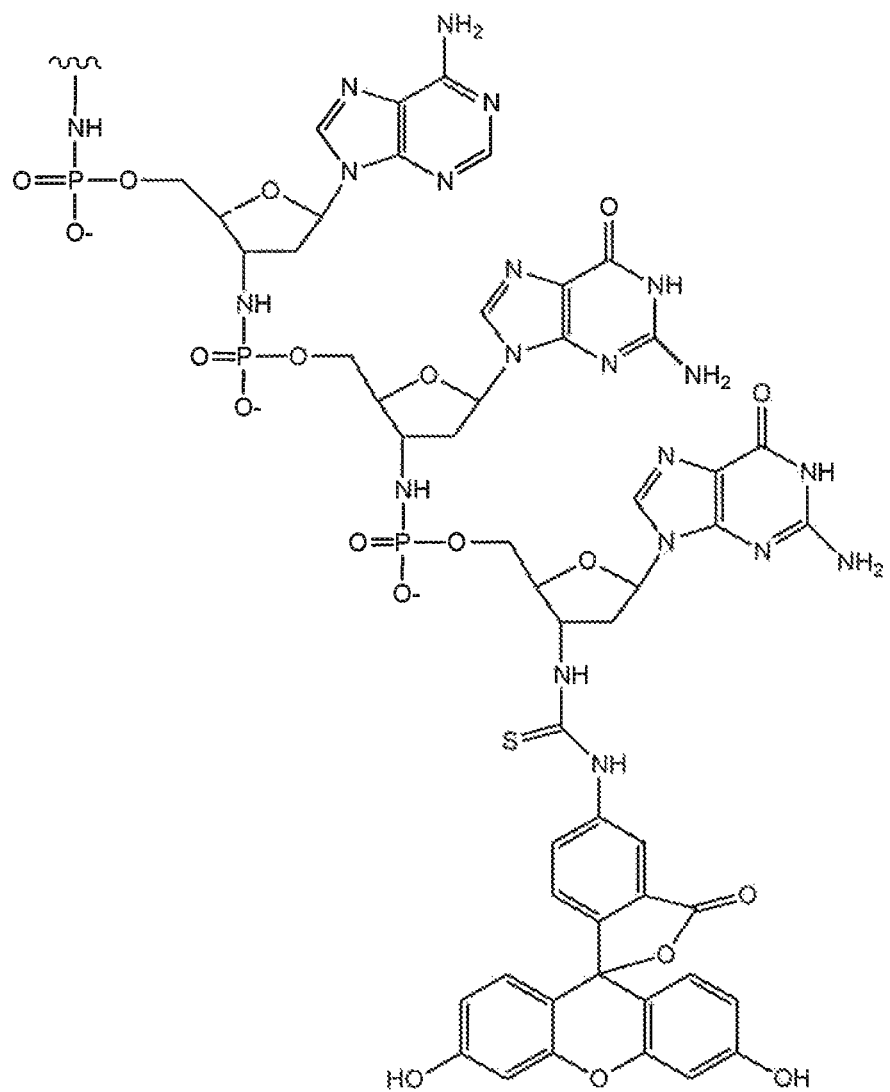
FIG. 1 shows the structure of an exemplary oligonucleotide conjugate of the invention wherein the polynucleotide AGG (SEQ ID NO.: 1) having phosphoramidate internucleoside linkages is attached to fluorescein via a thiourea group.

An "alkyl group" refers to an alkyl or substituted alkyl group having 1 to 20 carbon atoms, such as methyl, ethyl, propyl, and the like. Lower alkyl typically refers to $C_1$ to $C_5$. Intermediate alkyl typically refers to $C_6$ to $C_{10}$. An "acyl group" refers to a group having the structure RCO wherein R is an alkyl. A lower acyl is an acyl wherein R is a lower alkyl.

An "alkylamine" group refers to an alkyl group with an attached nitrogen, e.g., 1-methyl1-butylamine $(CH_3CHNH_2CH_2CH_2CH_3)$.

An "aryl group" refers to an aromatic ring group having 5-20 carbon atoms, such as phenyl, naphthyl, anthryl, or substituted aryl groups, such as, alkyl- or aryl-substitutions like tolyl, ethylphenyl, biphenylyl, etc. Also included are heterocyclic aromatic ring groups having one or more nitrogen, oxygen, or sulfur atoms in the ring.

"Oligonucleotide" refers to nucleoside subunit polymers having between about 2 and about 50 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→P5' thio-phosphoramidate, and phosphorothioate linkages. Further, "oligonucleotides" includes modifications, known to one skilled in the art, to the sugar backbone (e.g., ribose or deoxyribose subunits), the sugar (e.g., 2' substitutions), the base, and the 3' and 5' termini. In embodiments where the oligonucleotide moiety includes a plurality of intersubunit linkages, each linkage may be formed using the same chemistry or a mixture of linkage chemistries may be used. The term "polynucleotide", as used herein, has the same meaning as "oligonucleotide" and is used interchangeably with "oligonucleotide".

Whenever an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

As used herein, "nucleoside" includes the natural nucleosides, including 2'-deoxy and 2'-hydroxyl forms, e.g. as described in Komberg and Baker, DNA Replication, 2nd Ed. (Freeman, San Francisco, 1992), and analogs. "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, such as disclosed by Uhlmann and Peyman (Chemical Reviews, 90:543-584, 1990).

A "nucleobase" is defined herein to include (i) typical DNA and RNA nucleobases (uracil, thymine, adenine, guanine, and cytosine), (ii) modified nucleobases or nucleobase analogs (e.g., 5-methyl-cytosine, 5-bromouracil, or inosine) and (iii) nucleobase analogs. A nucleobase analog is a chemical whose molecular structure mimics that of a typical DNA or RNA base.

As used herein, "pyrimidine" means the pyrimidines occurring in natural nucleosides, including cytosine, thymine, and uracil, and analogs thereof, such as those containing oxy, methyl, propynyl, methoxy, hydroxyl, amino, thio, halo, and like, substituents. The term as used herein further includes pyrimidines with protection groups attached, such as $N_4$-benzoylcytosine. Further pyrimidine protection groups are disclosed by Beaucage and Iyer (Tetrahedron 48:223-2311, 1992).

As used herein, "purine" means the purines occurring in natural nucleosides, including adenine, guanine, and hypoxanthine, and analogs thereof, such as those containing oxy, methyl, propynyl, methoxy, hydroxyl, amino, thio, halo, and like, substituents. The term as used herein further includes purines with protection groups attached, such as $N_2$-benzoylguanine, $N_2$-isobutyrylguanine, $N_6$-benzoyladenine, and the like. Further purine protection groups are disclosed by Beaucage and Iyer (cited above).

As used herein, the term "protected" as a component of a chemical name refers to art-recognized protection groups for a particular moiety of a compound, e.g. "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like. Art-recognized protection groups include those described in the following references: Gait, editor, Oligonucleotide Synthesis: A Practical Approach (IRL Press, Oxford, 1984); Amarnath and Broom, Chemical Reviews, 77:183-217, 1977; Pon et al., Biotechniques, 6:768-775, 1988; Ohtsuka et al., Nucleic Acids Research, 10:6553-6570, 1982; Eckstein, editor, Oligonucleotides and Analogues: A Practical Approach (IRL Press, Oxford, 1991), Greene and Wuts, Protective Groups in Organic Synthesis, Second Edition, (John Wiley & Sons, New York, 1991), Narang, editor, Synthesis and Applications of DNA and RNA (Academic Press, New York, 1987), Beaucage and Iyer (cited above), and like references.

The term "halogen" or "halo" is used in its conventional sense to refer to a chloro, bromo, fluoro or iodo substituent. In the compounds described and claimed herein, halogen substituents are generally fluoro, bromo, or chloro, preferably fluoro or chloro.

B. Design and Synthesis of the Oligonucleotide Conjugates

The present invention is directed generally to compounds having the formula:

wherein A is an aromatic group, L is an optional linker (i.e. a linker or a direct bond), O is an oligonucleotide, n is an integer between 1 and 1+m where m is the total number of nucleosides comprising the oligonucleotide. Design of the compounds therefore requires the selection of three entities, A, L and O and the determination of the structural linkages between these entities.

Selection of O

The oligonucleotide sequence of O is selected such that it is complementary to the RNA sequence of the target telomerase, e.g., human telomerase. The RNA component of human telomerase has been sequenced (see Feng et al., Science 269 (5228), 1236-1241, 1995, sequence data also available on GenBank, Accession No. U86046). Within the human telomerase RNA ("hTR") sequence is a region identified as the "template region" that functions to specify the sequence of the telomeric repeats that telomerase adds to the chromosome ends; this template region is essential to the activity of the telomerase enzyme (see Chen et al., Cell 100:503-514, 2000; Kim et al, Proc. Nat'l. Acad. Sci, USA 98(14): 7982-7987, 2001). The template region is an 11 nucleotide region of sequence 5'-CUAACCCUAAC-3' (SEQ ID: 2) that has therefore been identified as a particularly suitable target for inhibitory oligonucleotides. Accordingly, while the selection of the oligonucleotide sequence of the O component of the oligonucleotide conjugates can be made from any region of the hTR sequence, selection of a sequence complementary to the template and/or adjacent regions of the hTR sequence is preferred. The sequence selected is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide O is thus selected to include a sequence of from 2 to 11 nucleotides exactly complementary to the template region of human telomerase RNA. Optimal telomerase inhibitory activity may be obtained when the full length of the oligonucleotide O is selected to be complementary to a part of the hTR template region sequence.

The length of the oligonucleotide O may vary from 2 to about 50 nucleosides. However, oligonucleotides of shorter lengths are preferred since shorter molecules are (a) more easily synthesized and may be produced at a lower cost and (b) likely to be more bio-available. Thus, in preferred embodiments the length of the oligonucleotide O components is from 4-15 nucleosides, and in particular embodiments from 4-8 nucleosides. The examples of oligonucleotide conjugates presented below show that lengths of O of 4-8 nucleosides have potent telomerase inhibition activity. Oligonucleotide conjugates of the invention include those having oligonucleotide (O) components containing 2, 3, 4, 5, 6, 7, 8, 9, and 10 or more nucleosides. One of skill in the art will appreciate that the selection of the sequence and length of the O component may also be affected by the selection of the L and A components of the conjugate. Simple experimentation using the standard telomerase activity assays described herein will facilitate selection of the optimal combinations. Preferably, the oligonucleotide conjugates will include a region of from 2 to 11 consecutive bases having a sequence complementary to all or part of the template region of human telomerase RNA. Illustrative oligonucleotide sequences that may be used in the conjugates of the invention include: TAGGGTTAGACAA (SEQ ID: 3); GTTAGGGTTAG (SEQ ID: 4); AGGGTTAG (SEQ ID: 5); GGGTTAG (SEQ ID: 6); GTTAGG (SEQ ID: 7); TTAGGG (SEQ ID: 8); TTA (SEQ ID: 9); AGGG (SEQ ID: 10); GGGTTA (SEQ ID: 11); TGAGTG (SEQ ID: 12); and GTAGGT (SEQ ID: 13).

The choice of the type of inter-nucleoside linkages used in the synthesis of the O component may be made from any of the available oligonucleotide chemistries, including but not limited to, phosphodiester, phosphotriester, methylphosphonate, P3'→N5' phosphoramidate, N3'→P5' phosphoramidate, N3'→P5' thio-phosphoramidate, and phosphorothioate linkages. Oligonucleotides having at least one N3'→P5' phosphoramidate or N3'→P5' thio-phosphoramidate linkage may have characteristics that provide advantages in the therapeutic context. Exemplary oligonucleotide linkages may be represented by the formula:

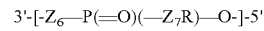

wherein $Z_6$ is O or NH; $Z_7$ is O or S; and R is selected from the group consisting of hydrogen, alkyl, aryl and salts thereof.

Methods for synthesizing oligonucleotides suitable for incorporation into the conjugates described herein are well known in the art. By way of example, oligonucleotide N3'→P5' thio-phosphoramidates for use in the invention may be synthesized using the phosphoramidite transfer methodology of Pongracz et al., Tet. Let. 40: 7661-7664, 1999). This synthetic strategy employs 3'-NH-trityl-protected 3'-aminonucleoside 5'-O-cyanoethyl-N,N-diisopropylaminophosphor-amidites which are processed through the steps of 1) detritylation, 2) coupling; 3) capping; 4) sulfurization. To achieve a step-wise sulfurization of the internucleaside phosphoramidite group formed after the coupling step, sulfurizing agents such as elemental sulfur $S_8$ or PADS (diphenylacetyldisulfide) or the commonly used Beaucage reagent -3H-1,2-benzodithiol-3-one 1,1 dioxide (Iyer et al., J. Organic Chemistry 55:4693-4699, 1990) can be used. The oligonucleotide syntheses may be performed (1 μmole synthesis scale) with a 1% solution of Beaucage reagent in anhydrous acetonitrile or 15% $S_8$ in $CS_2/Et_3N$, 99/1 (vol/vol) as the sulfurizing agent.

Chimeric N3'→P5' phosphoramidate-phosphorthioamidate oligonucleotides can be made by using an oxidation step(s) after the coupling step, which results in formation of a phosphoramidate internucleoside group. Similarly, phosphodiester-phosphorthioamidates can be made by using 5'-phosphoramidite-3'-O-DMTr-protected nucleotides as monomeric building blocks. These synthetic approaches are known in the art.

Selection of A

It is believed that the conjugates of the present invention bind to telomerase in two aspects, thereby inhibiting function of the enzyme. The first aspect of the binding is the base-pair complementarity between the nucleosides of hTR and the nucleosides of the oligonucleotide (O) component of the conjugate. The second aspect of the binding is the interaction between the telomerase protein component and the A component of the conjugate. A wide range of substituents may serve this second binding aspect provided by the A component which, as a matter of convenience, is referred to herein as an "aromatic" moiety. In this context, the term "aromatic" is used broadly to encompass, for example, polyaromatic hydrocarbons, mono- and poly-cyclic heteroaromatic systems and nucleobases (including modified nucleobases and nucleobase analogs).

Classes of suitable aromatic systems include intercalators, reporter molecules, chromophores, fluorophores and nucleobases (including nucleobase derivatives and nucleobase analogs). Particular examples of suitable A substituents include fluoresceins, rhodamines, coumarins, acridines, triphenyl carbons, anthraquinones and purine and pyrimidine nucleobases. Where the A moiety is selected to be a nucleobase, nucleobases capable of hydrogen-bonding are preferred, since hydrogen-bonding is expected to increase the stability of the interaction between the A moiety and the protein component of telomerase. Examples of nucleobases capable of hydrogen-nonding include adenine, guanine, cytosine, thymine and uracil.

Illustrative fluorophores are shown below:

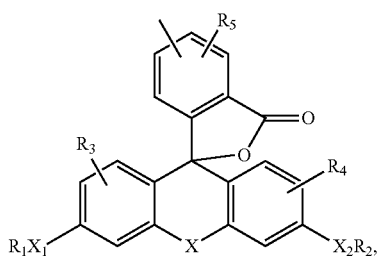

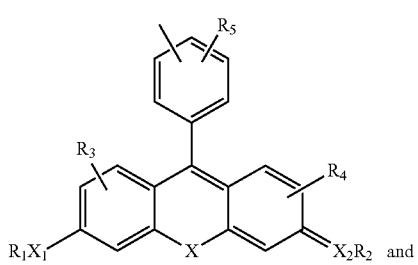

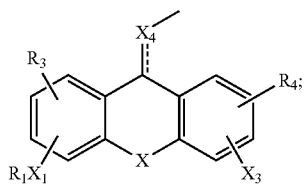

where X, $X_1$ and $X_2$ are independently selected from the group consisting of O, S, and N; $X_3$ is hydrogen, halogen, or alkyl; $X_4$ is C, N, O, or S; $R_1$ and $R_2$ are independently selected from the group consisting of H, methyl, ethyl, and propyl; and $R_3$, $R_4$ and $R_5$ are independently selected from the group consisting of H, hydroxyl, halogen, alkyl, aryl, carboxyl, and X-alkyl, and ⸾ is a single or a double bond.

Particular examples of suitable aromatic systems are fluorescein, having the formula:

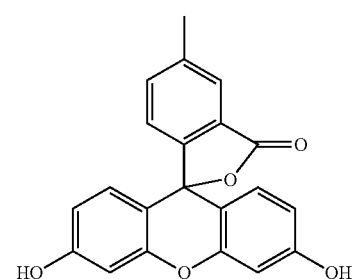 [SMILES: Cc1ccc2c(c1)C(=O)OC21c2ccc(O)cc2Oc2cc(O)ccc21]

N,N'-tetramethylrhodamine, having the formula:

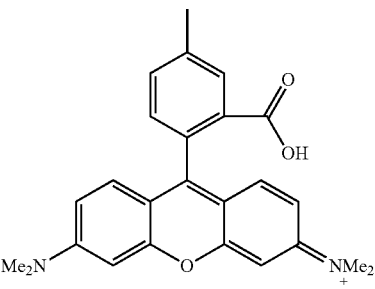

Trityl having the formula:

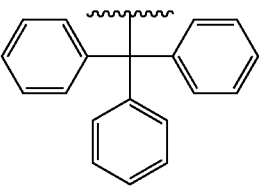 [SMILES: *C(c1ccccc1)(c1ccccc1)c1ccccc1]

And pyrene-butyric acid, having the formula:

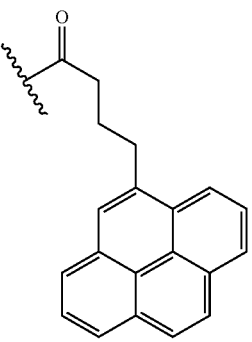 [SMILES: *C(=O)CCCc1cc2cccc3ccc4cccc1c4c32]

Examples of suitable A moieties which fall into the nucleobase class of A substituents include the nucleobases found in DNA and RNA, specifically the pyrimidines cytosine, thymine and uracil, and the purines adenine and guanine, the structures of which are well known. A wide range of modified nucleobases and nucleobase analogs are known in the art; widely available forms include halogen-, nitro- and hydroxy-substituted nucleobases, preferably substituted at the 2-, 6- or 8-positions, such as 2-chloroadenine, 6-thioguanine, 6-chloroguanine, 8-bromoadenine, 8-iodoadenine, 8-hydroxyguanine and 8-nitroguanine, and nucleobases with ring substitutions such as deaza nucleobases in which one or more nitrogen atoms in the heterocyclic ring is substituted for a carbon. Examples of ring-substituted nucleobase derivatives include 2,6-diaminopurines, 7-alkylpurines, 7-alkynylpurines and 7-deazapurines. When the A substitutent is selected to be a nucleobase, nucleobase analog or nucleobase derivative, it is preferred that the nucleobase be capable of hydrogen-bonding, thereby increasing the stability of the interaction between the A moiety and the protein component of telomerase.

Figure 3:
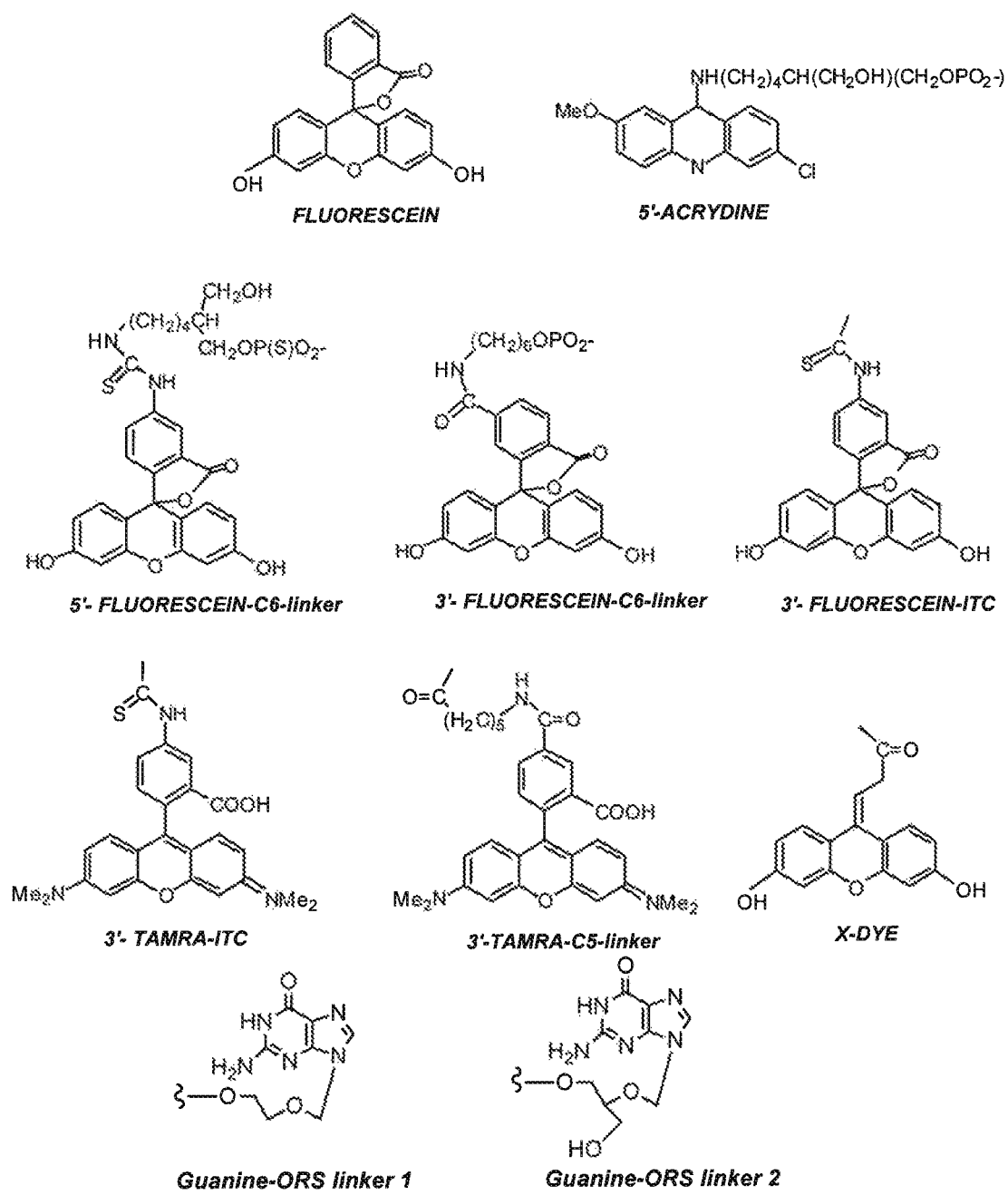
FIG. 3 shows the structures of exemplary aromatic systems having linker groups attached to them.

Other aromatic substituents (shown conjugated with linker (L) groups) are depicted in FIG. 3. "A" substituents that may be employed in the oligonucleotide conjugates of the present invention may be purchased from chemical reagent suppliers or synthesized using standard chemical synthesis procedures. As with the selection of the oligonucleotide (O) component, the activity of oligonucleotide conjugates having various A moieties may readily be determined using standard telomerase activity assays.

Selection of L

The linkage between the O and A components may be facilitated by the incorporation of a linker sequence. Such a sequence may serve not only to facilitate the chemical conjugation of the two moieties, but may also serve to increase the activity of the conjugate by conferring flexibility and thereby enhancing the availability of each moiety to bind to its target on the telomerase enzyme. Linkers may be conjugated directly to the sugar ring of the oligonucleotide O, or to the internucleoside backbone, such as the phosphodiester or phosphoramidate internucleoside linkages, or to the nucleobase of the oligonucleotide. A variety of linker groups may be utilized, depending on the selection of the A component. Exemplary linkers are the structures:

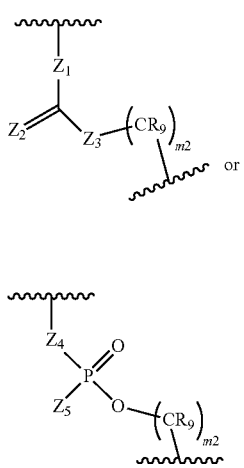

Type 1 linker or

Type 2 linker

Wherein:

$Z_1$, $Z_2$, and $Z_3$ are independently selected from the group consisting of O, S, and $NR_4$, wherein $R_4$ is H or lower alkyl and $Z_1$ and $Z_3$ can be direct bonds;

$Z_5$ is O or NH;

$Z_5$ is OR', SR', or methyl wherein R' is selected from the group consisting of hydrogen, alkyl, aryl and salts thereof;

$R_9$ is H, halogen or lower alkyl, and m2 is an integer from 0 to 10.

In instances where no linker group is desired, L is a direct bond between A and O.

One example of a Type 1 linker is the thiourea linker in which: $Z_1$=NH; $Z_2$=S; $Z_3$=NH; and m2=0 (i.e., there is no carbon between the $Z_3$=N substituent and the A moiety. A Type 1 thiourea linker is shown in the structure depicted in Illustration A in the Summary section above.

A representation of the structure of oligonucleotide conjugates having a Type 2 linker is shown below:

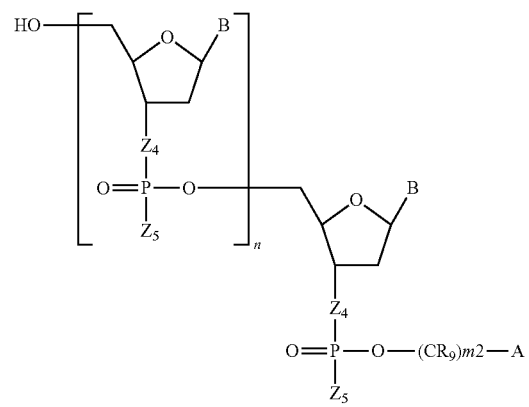

wherein each B is a base independently selected to be a purine or pyrimidine or an analog thereof such as uracil, thymine, adenine, guanine, cytosine, 5-methylcytosine, 5-bromouracil and inosine, A is the aromatic moiety and the linker shown linking the 3' sugar ring of O to the A moiety is a type 2 linker. From this arrangement, it is apparent that the definition of the Type 2 linker structure incorporates components of an internucleoside linkage. Reference to a "C5" or "C6" linker refers to a Type 1 or 2 linker in which m2=5 or 6.

Where the A moiety is a nucleobase, a preferred type of linker is the Type 3 linker, which may be conjugated directly to the 3' position of the 3' sugar ring of the oligonucleotide O:

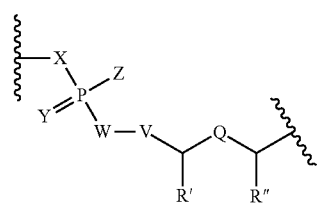

Wherein:

X=N or O

Y=O or S

Z=O or S

W=N, O, S or lower alkyl (preferably $CH_2$)

V is lower alkyl

Q=O, S or NR''', wherein R''' is H, lower alkyl or lower acyl

R' and R'' are independently=H, OH, alkyl (including substituted alkyl, preferably lower alkyl) or alkylamine.

Typically, a Type 3 linker is conjugated to the sugar ring of the 3' nucleobase of the oligonucleotide O.

Particularly preferred forms of the Type 3 linker are linkers that include phosphate groups conjugated to open ring sugars, thus resembling a modified oligonucleotide phosphate-sugar backbone. Examples of Type 3 linkers incorporating open ring sugar groups are Open Ring Sugar Linkers 1 and 2, which are illustrated below and are in the examples shown in Table 2 below:

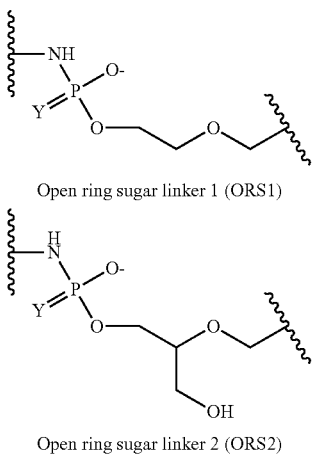

Open ring sugar linker 1 (ORS1)

Open ring sugar linker 2 (ORS2)

(As noted above, the Y substituent may be oxygen or sulfur and may be selected such that this substituent is consistent with the equivalent substituent in the internucleoside linkages of the oligonucleotide O. Thus, when O is selected to be a phosphoramidate oligonucleotide, Y may be selected to be oxygen, and when O is selected to be a thio-phosphoramidate oligonucleotide, Y may be selected to be sulfur.)

Notably, where the A moiety is selected to be guanine and the L moiety is Open Ring Sugar Linker 1 or 2, this combination produces acyclovir or ganciclovir, respectively, conjugated to the phosphate group, which in turn is then conjugated to the 3' sugar ring of the oligonucleotide O.

It will be apparent that another way of representing the linkage produced by linking a nucleobase to the 3' sugar of the oligonucleotide O using a Type 3 linker is to represent the phosphate group not as part of the Type 3 linker, but instead as the 3' internucleoside linkage of the oligonucleotide. In this instance, the structure may be represented as follows, with the modified Type 3 linker now referred to as a Type 4 linker, with substituents as described for the Type 3 linker above:

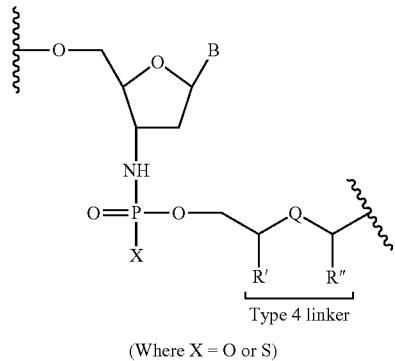

Type 4 linker (Where X = O or S)

In oligonucleotide conjugates of the invention represented by the formula $(A-L-)_n-O$, when A is selected to be a nucleobase, the formula is not intended to include the possibility that A-L simply represents an additional conventional nucleoside or nucleotide that is part of the oligonucleotide O. Rather, A-L represents a moiety that distinguishes the oligonucleotide conjugates of the invention both in structure and in function from conventional known oligonucleotides.

Thus, in particular embodiments, when A is a nucleobase, L should not include a closed ring sugar group, of the type that is found in nucleobase linkages in conventional oligonucleotides. In part, this reflects the preference that the linker L in conjugates in which A is a nucleobase should be a flexible linker, nucleobase linkages employing closed ring sugar groups used in conventional oligonucleotides are not considered to produce flexible linkers. As used herein the phrase "closed ring sugar group" includes heterocyclic 5 and 6 member closed ring sugar groups described in the art for use as nucleobase linkages in oligonucleotides, including ribose and arabinose and known derivatives of these sugars which include a 5 or 6 member closed ring, such as ribose, deoxyribose, 2'-O methylribose and 2'-O fluororibose.

In other embodiments, the oligonucleotide conjugates of the invention are distinguished from conventional oligonucleotides in that the linker L is selected so that it is not the same as one or more inter-nucleobase linkages found in the oligonucleotide O. In this context, it will be appreciated that reference to the inter-nucleobase linkages found in the oligonucleotide O encompasses both the sugar moiety and the associated phosphate-based moiety that join the nucleobases of the oligonucleotide. Thus, in this embodiment, the oligonucleotide conjugates of the invention may be represented as $(A-L-)_n-O$, wherein A is a nucleobase, n is an integer between 1 and m+1, m is the total number of nucleosides in O, O is an oligonucleotide that comprises m nucleobases and m−1 inter-nucleobase linkages L', and L is a linker that is not the same as any L' found in the oligonucleotide O. An example of such a conjugate in which m=4 is as follows: $A-L-B^1-L'-B^2-L'-B^3-L'-B^4$ wherein A is a nucleobase, $B^1$, $B^2$, $B^3$ and $B^4$ are independently selected nucleobases, L and L' are linkers, wherein L is not the same as L'.

It is important to note that many different linkers may be used in the present invention to join aromatic A groups to the oligonucleotide group O. The foregoing linkers are illustrative only.

Arrangement of Components

As implied by the structure $(A-L-)_n-O$, wherein A is an aromatic group, L is an optional linker, O is an oligonucleotide, n is an integer between 1 and 1+m where m is the total number of nucleosides comprising the oligonucleotide, multiple A substituents may be conjugated to the oligonucleotide. Moreover, the A substituents may be attached to the oligonucleotide, optionally through a linker L, at the 3'-position, at the 5'-position, on the intersubunit linkage, on the sugar ring, on the base, or combinations thereof. However, in typical embodiments, one or two A substituents are used (i.e., n=1 or 2), and these are generally attached (through L) to the 3'-position or the 5'-position of the terminal sugar residue of the oligonucleotide O, or to the intersubunit linkage that is attached to the sugar at that point. When A is selected to be a nucleobase, it is preferably conjugated to the 3' terminus of the oligonucleotide O in order to enhance telomerase inhibitory activity, and most preferably, is conjugated, via a linker L, to the 3' position of the sugar of the 3' terminal nucleoside.

Figure 2:
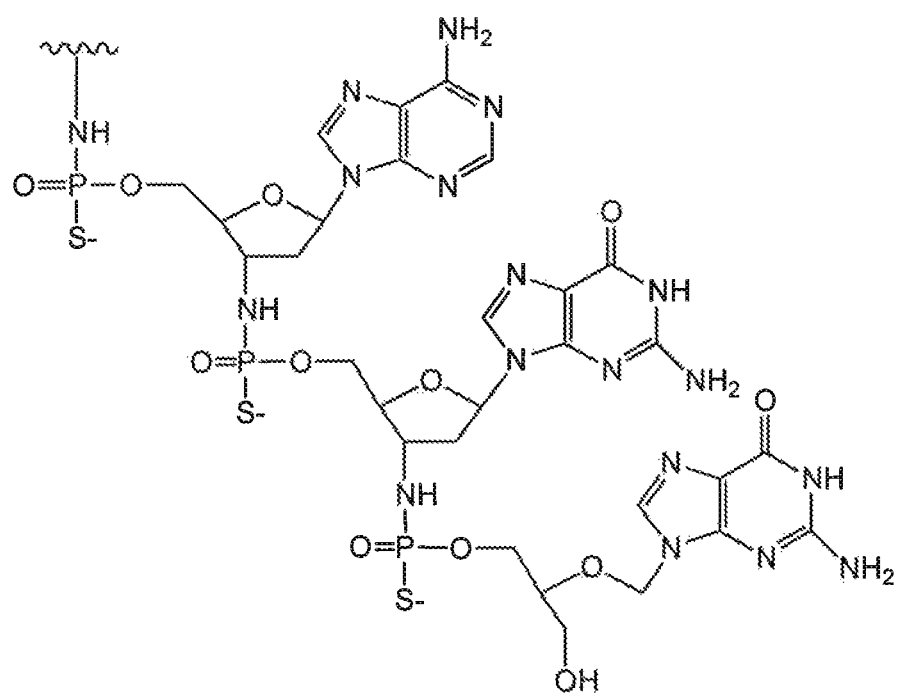
FIG. 2 shows the structure of an exemplary oligonucleotide conjugate of the invention wherein the polynucleotide AGG (SEQ ID NO:1) having thiophosphoramidate internucleoside linkages is attached to guanine via a Type 3 Linker (specifically, an open-ring sugar linker, ORS2).

FIG. 1 illustrates an example in which the A substituent is fluorescein attached to the 3'-position of the oligonucleotide via a thiourea linker L. FIG. 2 illustrates an example in which the A substituent is guanine attached to the 3' terminal intersubunit linkage of the oligonucleotide via an open ring sugar linker L. Where two or more A substituents are utilized, the A substituents are independently selected. As with the selection of all of the components, the design of the conjugate can readily be tested by performing standard telomerase activity assays as described below.

In particular embodiments, the integer n is selected to be 1, such that the structure of the oligonucleotide conjugate can be represented as:

A-L-O and wherein O is preferably an oligonucleotide that comprises a sequence of from 2 to 11 nucleotides exactly complementary to a sequence within the template region of human telomerase RNA.

In such embodiments, when A is selected to be a nucleobase, it is preferably conjugated to the 3' position of the 3' terminal sugar of the oligonucleotide O. While various chemistries may be employed for the internucleoside linkages within O, phosphorothioate, phosphoramidate, and thiophosphoramidate linkages are particularly desirable. Telomerase inhibition activity may be particularly good when the sequence of the oligonucleotide O is selected such that it has a 3' terminus of GGG, since oligonucleotides of this type may form highly stable interactions with the telomerase enzyme. Exemplary oligonucleotide sequences include TTAGGG (SEQ ID: 8) and AGGG (SEQ ID: 10). Selection of a flexible linker, such as a Type 3 linker, preferably a Open Sugar Ring Linker 1 or Open Sugar Ring Linker 2 may also enhance telomerase inhibitory activity, as may the selection of a purine nucleobase, in particular guanine, as the A moiety.

In another embodiment of the invention, where the oligonucleotide conjugate $(A-L)_n$-O is designed so that n>1, a first selected A substituent is covalently conjugated to the oligonucleotide O, and other A substituents are sequentially linked, optionally through a linker, to the first A substituent. An example of such a conjugate is TAA-ORS2-G*G*G* as shown in Table 2, in which a first guanine nucleobase is linked through a Type 3 linker (specifically an Open Ring Sugar Linker 2) to the 3' position of the 3' terminal sugar ring of the oligonucleotide O. A second guanine nucleobase is then linked to the first, also through an Open Ring Sugar Linker 2, and the third is then linked to the second in a similar manner.

Synthesis of the Oligonucleotide Conjugates

The aromatic substituent can be covalently linked to the oligonucleotide using standard chemical syntheses. Typically, the nucleophilic sites on the oligonucleotide are first protected and the desired site of attachment is selectively deprotected. The oligonucleotide is then reacted with, for example in the case of the aromatic substituent being fluorescein, fluorescein containing a reactive group such as isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal or aldehyde, to yield a modified oligonucleotide in which fluorescein is bound to the oligonucleotide, preferably through a thiourea or an amide group, as shown in the scheme below:

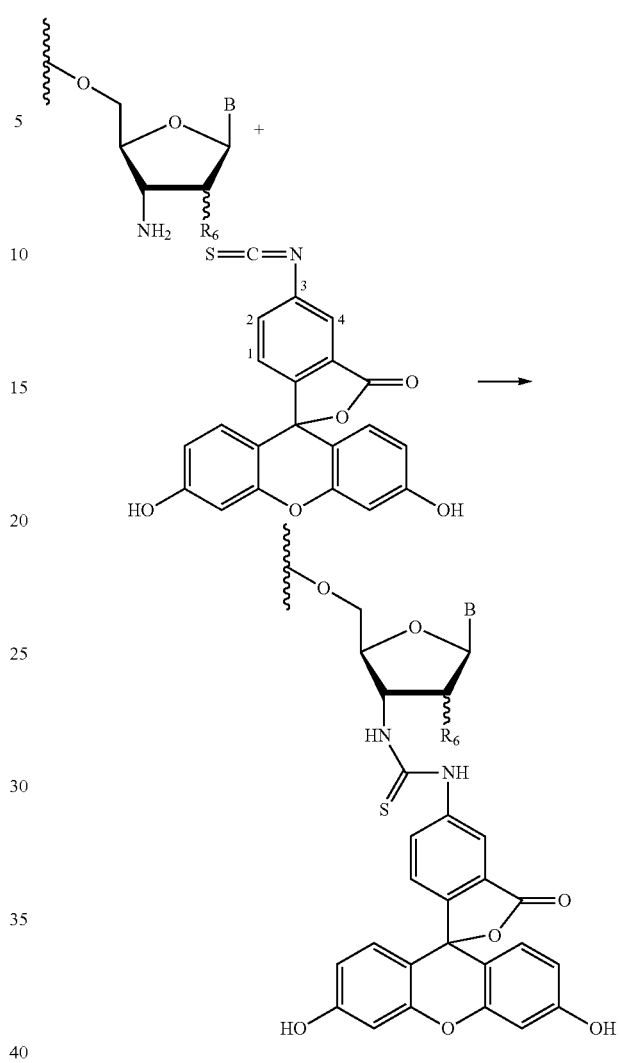

The linker L may be joined to the aromatic system A at position 1, 2, 3, or 4. Preferably, L is joined to A at the 3 position.

Alternatively, the linker can first be converted into a phosphoramidite followed by coupling to the oligonucleotide, as described in U.S. Pat. No. 5,583,236 to Brush. Typically, when the aromatic system is fluorescein, commercially available fluorescein 3-isothiocyanate diacetate is reacted sequentially with aminopenta-6-ol and then a phosphitylating reagent to yield a phosphoramidite linked to fluorescein via a five carbon chain and a thiourea group, as shown below:

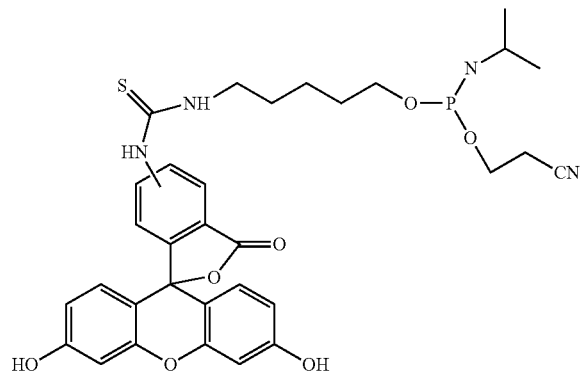

Some examples of a linker L joined to a suitable aromatic system A are illustrated in FIG. 3.

Where the A moiety is a nucleobase, the same general synthetic approaches are employed. Nucleobases may be purchased with groups already attached that are suitable as linkers or which may be readily modified to produce suitable linkers. For example, guanine may conveniently be purchased with attached open ring sugars in the form of acyclovir or ganciclovir, in which the conjugated open ring sugar forms a Type 4 linker as shown above. The open ring sugar is then phosphitylated to form a phosphoramidate (with other reactive groups present in the linker being protected with an appropriate protecting group). The resultant phosphoramidate is then coupled to the oligonucleotide using standard procedures on an automated DNA synthesizer, as described above. Subsequent modification of the linker (e.g., sulfurization to produce a thiophosphoramidate moiety) is performed using standard chemistry.

Telomerase Inhibition Assays

The conjugates of the present invention may be used to inhibit or reduce telomerase enzyme activity and/or proliferation of cells having telomerase activity. In these contexts, inhibition or reduction of the enzyme activity or cell proliferation refer to a lower level of the measured activity relative to a control experiment in which the enzyme or cells are not treated with the conjugate. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications.

Methods for measuring telomerase activity, and the use of such methods to determine the telomerase inhibitory activity of compounds are well known. For example, the TRAP assay is a standard assay method for measuring telomerase activity in a cell extract system and has been widely used in the search for telomerase inhibiting compounds (Kim et al., Science 266:2011, 1997; Weinrich et al., Nature Genetics 17:498, 1997). The TRAP assay measures the amount of radioactive nucleotides incorporated into elongation products (polynucleotides) formed by nucleotide addition to a telomerase substrate or primer. The radioactivity incorporated can be measured as the intensity of a band on a detection screen (e.g. a Phosphorimager screen) exposed to a gel on which the radioactive products are separated. The TRAP assay is also described in detail in U.S. Pat. Nos. 5,629,154, 5,837,453 and 5,863,726, and its use in testing the activity of telomerase inhibitory compounds is described in various publications including WO 01/18015. In addition, the following kits are available commercially for research purposes for measuring telomerase activity: TRAPeze® XK Telomerase Detection Kit (Cat. s7707; Intergen Co., Purchase N.Y.); and TeloTAGGG Telomerase PCR ELISA plus (Cat. 2,013,89; Roche Diagnostics, Indianapolis Ind.).

Typically, the ability of the conjugates of the invention to inhibit telomerase activity will first be confirmed by performing a biochemical telomerase activity assay, such as the TRAP assay, and comparing the results obtained in the presence of the conjugate with results obtained from a control experiment performed without the conjugate. Such data permit the calculation of an $IC_{50}$ value for the conjugate (the concentration of the test compound at which the observed activity for a sample preparation is observed to fall one-half of its original or a control value). Using such methods, $IC_{50}$ values for several of the oligonucleotide conjugates of the present invention were determined, and found to be below 10 μM.

In addition, the specificity of the oligonucleotide conjugates for telomerase RNA can be determined by performing hybridization tests with and comparing their activity ($IC_{50}$) with respect to telomerase and to other enzymes known to have essential RNA components, such as ribonuclease P. Compounds having lower $IC_{50}$ values for telomerase as compared to the $IC_{50}$ values toward the other enzymes being screened are said to possess specificity for telomerase.

Having confirmed that a particular conjugate is an effective telomerase inhibitor using a biochemical assay, it may then be desirable to ascertain the ability of the conjugate to inhibit telomerase activity in cells. Oligonucleotide conjugates that effectively inhibit telomerase activity in cells will, like other known telomerase-inhibiting compounds, induce crisis in telomerase-positive cell lines. Cell lines that are suitable for such assays include HME50-5E human breast epithelial cells, and the ovarian tumor cell lines OVCAR-5 and SK-OV-3. Importantly however, in normal human cells used as a control, such as BJ cells of fibroblast origin, the observed reduction in telomere length is expected to be no different from untreated cells. In selecting an oligonucleotide conjugate of the invention for therapeutic applications, one would typically select a conjugate that produced no significant cytotoxic effects at concentrations below about 20 μM in normal cells. Testing the ability of a candidate compound to inhibit telomerase in cell-based assays is also routine, and is described in WO 01/18015, Herbert et al., Oncogene, 21: 638-642, 2002; Gryaznov et al., Nucleosides, Nucleotides and Nucleic Acids, 20: 401-410, 2001; Izbika et al., Cancer Res., 59:639-644, 1999; Shammas & Corey Oncogene 18: 6191-6200, 1999; and Pitts & Corey, Porc. Nat'l. Acad. Sci. USA, 95:11549-11554, 1998.

Confirmation of the ability of an oligonucleotide conjugate to inhibit tumor cell growth in vivo can be obtained using established xenograft models of human tumors, in which the test conjugate is administered either directly to the tumor site or systemically, and the growth of the tumor is followed by physical measurement. Animals treated with oligonucleotide conjugates of the invention are expected to have tumor masses that, on average, may increase for a period following the initial dosing, but will begin to shrink in mass with continuing treatment. In contrast, untreated control mice are expected to have tumor masses that continue to increase. Examples of such xenograft models in screening for cancer therapeutics are described in Scorski et al., Proc. Nat'l. Acad. Sci. USA, 94: 3966-3971, 1997; and Damm et a., EMBO J., 20:6958-6968, 2001.

C. Formulation of Oligonucleotide Conjugates

The present invention provides oligonucleotide conjugates that can specifically and potently inhibit telomerase activity, and which may therefore be used to inhibit the proliferation of telomerase-positive cells, such as tumor cells. A very wide variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and circulating tumors (such as leukemia and lymphoma). Accordingly, the oligonucleotide conjugates provided herein may provide a broadly useful in treating a wide range of malignancies. More importantly, the oligonucleotide conjugates of the present invention can be effective in providing treatments that discriminate between malignant and normal cells to a high degree, avoiding many of the deleterious side-effects present with most current chemotherapeutic regimes which rely on agents that kill dividing cells indiscriminately. One aspect of the invention therefore is a method of treating cancer in a patient, comprising administering to the patient a therapeutically effective dose of an oligonucleotide conjugate of the present invention. Telomerase inhibitors, including oligonucleotide conjugates of the invention, may be employed in conjunction with other cancer treatment approaches, including surgical removal of primary tumors, chemotherapeutic agents and radiation treatment.

For therapeutic application, an oligonucleotide conjugate of the invention will be formulated in a therapeutically effective amount with a pharmaceutically acceptable carrier. One or more oligonucleotide conjugates (having different base sequences or linkages) may be included in any given formulation. The pharmaceutical carrier may be solid or liquid. Liquid carriers can be used in the preparation of solutions, emulsions, suspensions and pressurized compositions. The modified oligonucleotides are dissolved or suspended in a pharmaceutically acceptable liquid excipient. Suitable examples of liquid carriers for parenteral administration of the oligonucleotides preparations include water (partially containing additives, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and *arachis* oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration of the oligonucleotides, the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. The oligonucleotides can also be administered intravascularly or via a vascular stent.

The liquid carrier for pressurized compositions can be halogenated hydrocarbon or other pharmaceutically acceptable propellant. Such pressurized compositions may also be lipid encapsulated for delivery via inhalation. For administration by intranasal or intrabronchial inhalation or insufflation, the oligonucleotides may be formulated into an aqueous or partially aqueous solution, which can then be utilized in the form of an aerosol.

The oligonucleotide conjugates may be administered topically as a solution, cream, or lotion, by formulation with pharmaceutically acceptable vehicles containing the active compound.

The pharmaceutical compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleotides of the present invention may include carriers, lubricants, diluents, thickeners, flavoring agents, emulsifiers, dispersing aids or binders. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Pharmaceutical compositions and/or formulations comprising the oligonucleotides of the present invention may also include cellular and tissue penetration enhancing agent. Penetration enhancing agents that may be employed include, for example, fatty acids, bile salts, chelating agents, surfactants and non-surfactants (Lee et al., Critical Reviews in Therapeutic Drug Carrier Systems, 1991, 8, 91-192; Muranishi, Critical Reviews in Therapeutic Drug Carrier Systems, 1990, 7, 1-33). Liposome carriers may also be used as penetration agents. The use of liposomes to facilitate cellular uptake is described, for example, in U.S. Pat. No. 4,897,355 and U.S. Pat. No. 4,394,448. Numerous publications describe the formulation and preparation of liposomes. Fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Such penetration enhancers may be simply added to the formulation, or may be covalently conjugated to the oligonucleotide conjugates described herein. Methods of conjugating oligonucleotides to lipid moieties are described in, for example, Mishra et al., (1995) Biochemica et Biophysica Acta, 1264: 229-237). The use of synthetic polymers for the delivery of therapeutic oligonucleotides is described in Chirila et al. (2002) Biomaterials 23: 321-342. Oligonucleotide conjugates of the invention may thus be further modified by formulation with a moiety designed to enhance cellular and or tissue penetration (in general terms, a penetration enhancer). In particular embodiments, the oligonucleotide conjugates of the invention may further comprise a covalently linked penetration enhancing agent.

Complex formulations comprising one or more penetration enhancing agents may be used. For example, bile salts may be used in combination with fatty acids to make complex formulations. Exemplary combinations include chenodeoxycholic acid (CDCA), generally used at concentrations of about 0.5 to 2%, combined with sodium caprate or sodium laurate, generally used at concentrations of about 0.5 to 5%.

Pharmaceutical compositions and/or formulations comprising the oligonucleotides of the present invention may also include chelating agents, surfactants and non-surfactants. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Surfactants include, for example, sodium lauryl sulfate, polyoxyethylene-9-lauryl ether and polyoxyethylene-20-cetyl ether; and perfluorochemical emulsions, such as FC-43. Non-surfactants include, for example, unsaturated cyclic ureas, 1-alkyl- and 1-alkenylazacyclo-alkanone derivatives, and non-steroidal anti-inflammatory agents such as diclofenac sodium, indomethacin and phenylbutazone.

Thus, in another aspect of the invention, there is provided a method of formulating a pharmaceutical composition, the method comprising providing an oligonucleotide conjugate compound as described herein, and combining the compound with a pharmaceutically acceptable excipient. Preferably the oligonucleotide conjugate is provided at pharmaceutical purity, as defined below. The method may further comprise adding to the oligonucleotide conjugate compound, either before or after the addition of the excipient, a penetration enhancing agent. Exemplary penetration enhancing agents are listed above. In particular embodiments, the penetration enhancing agent may be covalently linked to the oligonucleotide conjugate.

The pharmaceutical composition will typically comply with pharmaceutical purity standards. For use as an active ingredient in a pharmaceutical preparation, an oligonucleotide of this invention is generally purified away from other reactive or potentially immunogenic components present in the mixture in which they are prepared. Typically, to achieve pharmaceutical purity, each active ingredient is provided in at least about 90% homogeneity, and more preferably 95% or 99% homogeneity, as determined by functional assay, chromatography, or gel electrophoresis. The active ingredient is then compounded into a medicament in accordance with generally accepted procedures for the preparation of pharmaceutical preparations. Thus, in the present invention, providing the oligonucleotide conjugate compounds at pharmaceutical purity requires that the compound be provided at at least about 90% homogeneity, and more preferably at least 95% or 99% homogeneity.

The pharmaceutical composition will also typically be aliquoted and packaged in either single dose or multi-dose units. The dosage requirements for treatment with the oligonucleotide conjugates vary with the particular compositions employed, the route of administration, the severity of the symptoms presented, the form of the oligonucleotides and the particular subject being treated.

Pharmaceutical compositions of the invention can be administered to a subject in a formulation and in an amount effective to achieve a clinically desirable result. For the treatment of cancer, desirable results include reduction in tumor mass (as determined by palpation or imaging; e.g., by radiography, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor-specific markers such as serum PSA), and improvement in quality of life (as determined by clinical assessment, e.g., Karnofsky score).

The amount of oligonucleotide per dose and the number of doses required to achieve such effects can be determined empirically using in vitro tests and animal models. An appropriate range for testing can be estimated from the 50% inhibitory concentration determined with isolated telomerase or cultured cells. Preparations of isolated telomerase can be obtained according to U.S. Pat. No. 5,968,506. Typically, the formulation and route of administration will provide a local concentration at the disease site of between 1 µM and 1 nM of the oligonucleotide conjugate.

In general, the oligonucleotide conjugates are administered at a concentration that affords effective results without causing any harmful or deleterious side effects. Such a concentration can be achieved by administration of either a single unit dose, or by the administration of the dose divided into convenient subunits at suitable intervals throughout the day.

EXAMPLE 1

General Methods $^{31}$P NMR spectra were obtained on a Varian 400 Mhz spectrometer. $^{31}$P NMR spectra were referenced against 85% aqueous phosphoric acid. Anion exchange HPLC was performed using a Dionex DX 500 Chromatography System, with a Pharmacia Biotech Mono Q HR 5/5 or 10/16 ion exchange columns. Mass spectral analysis was performed by Mass Consortium, San Diego, Calif. MALDI-TOF analysis of oligonucleotides was obtained using a PerSpective Biosystems Voyager Elite mass spectrometer with delayed extraction. Thermal dissociation experiments were conducted on a Cary Bio 100 UV-Vis spectrometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic anhydride, 1,2-dichloroethane, and dioxane were purchased from Aldrich (Milwaukee, Wis.).

All non-thio-phosphoramidate oligonucleotides were synthesized on an ABI 392 or 394 DNA synthesizer using standard protocols for the phosphoramidite based coupling approach (Caruthers, Acc. Chem. Res., 24:278-284, 1991). The chain assembly cycle for the synthesis of oligonucleotide phosphoramidates was the following: (i) detritylation, 3% trichloroaceticacid in dichloromethane, 1 min; (ii) coupling, 0.1 M phosphoramidite and 0.45 M tetrazole in acetonitrile, 10 min; (iii) capping, 0.5 M isobutyic anhydride in THF/lutidine, 1/1, v/v, 15 sec; and (iv) oxidation, 0.1 M iodine in THF/pyridine/water, 10/10/1, v/v/v, 30 sec.

Chemical steps within the cycle were followed by acetonitrile washing and flushing with dry argon for 0.2-0.4 min. Cleavage from the support and removal of base and phosphoramidate protecting groups was achieved by treatment with ammonia/EtOH, 3/1, v/v, for 6 h at 55° C. The oligonucleotides were concentrated to dryness in vacuo after which the 2'-t-butyldimethylsilyl groups were removed (if present) by treatment with 1M TBAF in THF for 4-16 h at 25° C. The reaction mixtures were diluted with water and filtered through a 0.45 nylon acrodisc (from Gelman Sciences, Ann Arbor, Mich.). Oligonucleotides were then analyzed and purified by IE HPLC and finally desalted using gel filtration on a Pharmacia NAP-5 or NAP-25 column. Gradient conditions for IE HPLC: solvent A (10 mM NaOH), solvent B (10 mM NaOH and 1.5 M NaCl); solvent A for 3 min then a linear gradient 0-80% solvent B within 50 min.

EXAMPLE 2

Synthesis of Oligoribonucleotide N3'→P5' Phosphoramidates

It was previously reported that homopurine and homopyrimidine oligoribonucleotide N3'→P5' phosphoramidates could be efficiently assembled on a solid phase support using a phosphoramidite transfer reaction (Gryaznov, et al. (1998) Nucleic Acids Res., 26:4160-4167). We found that this methodology works equally well for the synthesis of heterobased phosphoramidate oligoribonucleotides containing all four natural bases as well as thymidine and 2,4-diaminopurine (D). Each of the prepared oligoribonucleotide N3'→P5' phosphoramidites were synthesized starting from the 5'-end using a support-bound 2'-deoxy-3'-aminonucleoside as the 5'-terminal residue. Coupling steps involved exchange of the diisopropylamino group of the approaching 5'-O-phosphoramidite for the 3'-amino group of the support bound nucleoside. Standard RNA synthesis coupling times (10 min) and activator (1H-tetrazole) were used for each synthetic cycle. Unreacted 3'-amino groups were then capped with isobutyric anhydride, after which oxidation of the internucleotide phosphoramidite diester linkage into the phosphoramidate group was carried out with aqueous iodine. Subsequent detritylation of the 3'-amino group of the added residue enabled additional chain elongation steps to be repeated for the construction of the desired oligoribonucleotide phosphoramidates. The resin bound compounds were then deprotected and cleaved from the support by treatment with ammonia/ethanol solution. Removal of 2'-O-t-butyldimethylsilyl groups was accomplished using 1 M TBAF in THF after which the fully deprotected oligoribonucleotide phosphoramidates were analyzed and isolated using IE. The mixed base 9-13-mer oligoribonucleotide phosphoramidates were synthesized with step-wise coupling yields of about 96-98%, as judged by MMTr assays. The oligonucleotides were characterized by both $^{31}$P NMR and MALDI-TOF mass spectra analysis.

EXAMPLE 3

Synthesis of Oligonucleotide N3'→P5' Thio-phosphoramidates

Oligonucleotide N3'→P5' thio-phosphoramidates were prepared by the amidite transfer reaction on an ABI 394 synthesizer. The fully protected monomer building blocks were 3'-aminotrityl nucleoside-5'-(2-cyanoethyl-N,N-diisopropyl)phosphoramidite where nucleoside is 3'-deoxythymidine, 2',3'-dideoxy-N$^2$-isobutyryl-guanosine, 2',3'-dideoxy-N$^6$-benzoyl-adenosine or 2',3'-dideoxy-N$^4$-benzoyl-cytidine. 5'-Succinyl-3'-aminotrityl-2',3'-dideoxy nucleosides were coupled with an amino group containing long chain controlled pore glass (LCAA-CPG) and used as the solid support. The synthesis was performed in the direction of 5' to 3'. The following protocol was used for the assembly of oligonucleotide N3'→P5' thio-phosphoramidates: (i) detritylation, 3% dichloroacetic acid in dichloromethane; (ii) coupling, 0.1 M phosphoramidite and 0.45 M tetrazole in acetonitrile, 25 sec; (iii) capping, isobutyric anhydride/2,6-lutidine/THF 1/1/8 v/v/v as Cap A and standard Cap B solution; (iv) sulfurization, 0.1M solution of phenylacetyl disulfide (PADS) in acetonitrile:2,6-lutidine 1:1 mixture, 5 mins. The oligonucleotide thio-phosphoramidates were cleaved from the solid support and deprotected with concentrated aqueous ammonia. The compounds were analyzed and purified by HPLC. Ion exchange (IE) HPLC was performed using DIONEX DNAPac™ ion exchange column at pH 12 (10 mM NaOH) with a 1%/min linear gradient of 10 mM NaOH in 1.5 M NaCl and a flow rate of 1 ml/min. The products were desalted on Sephadex NAP-5 gel filtration columns (Pharmacia) and lyophilized in vacuo. $^{31}$P NMR experiments were performed in deuterium oxide to analyze the extent of sulfurization analysis ($^{31}$P NMR δ, ppm 58, 60 broad signals for Rp-, Sp-isomers).

Oligonucleotide thio-phosphoramidate 5'-GTTAGGGT-TAG-3' (SEQ ID NO.: 14) was synthesized the following way: An ABI Model 394 synthesizer was set up with 0.1M solutions of 3'-tritylamino-2',3'-dideoxy-N$^6$-benzoyl-adenosine (N$^2$-isobutyryl-guanosine, and thymidine) 5'-(2-cyanoethyl-N,N-diisopropyl)phosphoramidites. The reagent bottle of station #10 was filled with neat carbon disulfide and reagent bottle #15 was filled with a solution of 15% S$_8$ in carbon disulfide containing 1% triethylamine. As the activator the commercially available 0.45 M solution of tetrazole in acetonitrile was used. Cap A solution (station #11) was replaced by tetrahydrofuran/isobutyric anhydride/2,6-lutidine 8/1/1 v/v/v solution. Cap B was also the commercially available reagent. A new function was created to deliver carbon disulfide from station #10 to the column. The default sulfur synthesis cycle was modified the following way: sulfurization time was set at 5 mins. The synthesis column was filled with 1 μmole solid support N$^2$-isobutyryl-3'-(trityl)amino-2',3'-dideoxyguanosine-5'-succinyl-loaded CPG (controlled pore glass). The sequence of the compound was programmed as GATTGGGATTG (5'→3') (SEQ ID NO: 15). The trityl group was removed at end of the synthesis. The solid support was removed from the column and treated with 1 ml concentrated aqueous ammonia at 55° C. for 6 hr in a tightly closed glass vial. After filtration most of the ammonia was evaporated and the remaining solution was desalted using Sephadex™ NAP-5 gel filtration columns (Pharmacia) followed by lyophilization in vacuo. The product was analyzed and purified as described above.

EXAMPLE 4

Conjugation of Fluorescein to 3'-Amino or 5'-Amino Oligonucleotides

The reaction was conducted in 1.5 mL Eppendorff test tub, where ~10-20 OD of an oligonucleotide with free amino group was dissolved in 100 uL of 0.1 sodium-bicarbonate buffer, pH 8, and 50 uL of DMSO. Then ~1 mg of FITC (from Aldrich) was added to the solution, and the reaction mixture was shaken by vortexing for 1-2 minutes. The reaction mixture was heated to 55° C. for 30 minutes, and than left over night at room temperature in darkness. The oligonucleotide product was precipitated in the same test tube by the addition of 1.2 mL of EtOH, at −18° C. for 1 hour. The precipitate was separated from supernatant, and repricipitated twice with EtOH from 100 uL of 1 M NaCl.

The obtained oligonucleotide conjugate was then analyzed and purified if needed by RP HPLC.

Yields of the oligonucletide conjugates with FITC were 85-95%.

EXAMPLE 5

Conjugation of Ganciclovir to 3'-Amino or 5'-Amino Oligonucleotides

A 0.1 M solution of mono-O-dimethoxytrityl ganciclovir-O—CE-phosphoramidite in anhydrous acetonitrile was placed in an ABI Model 394 synthesizer using one of the extra stations for phosphoramidites. The synthesis and subsequent work up was carried out the same way as described in Examples 2 and 3. Purity of the conjugated oligonucleotide was assessed by ion exchange HPLC.

EXAMPLE 6

Preparation of Affinity Purified Extract Having Telomerase Activity

Extracts used for screening telomerase inhibitors were routinely prepared from 293 cells over-expressing the protein catalytic subunit of telomerase (hTERT). These cells were found to have 2-5 fold more telomerase activity than parental 293 cells. 200 ml of packed cells (harvested from about 100 liters of culture) were resuspended in an equal volume of hypotonic buffer (10 mM Hepes pH 7.9, 1 mM MgCl$_2$, 1 mM DTT, 20 mM KCl, 1 mM PMSF) and lysed using a dounce homogenizer. The glycerol concentration was adjusted to 10% and NaCl was slowly added to give a final concentration of 0.3 M. The lysed cells were stirred for 30 min and then pelleted at 100,000×g for 1 hr. Solid ammonium sulfate was added to the S100 supernatant to reach 42% saturation. The material was centrifuged; the pellet was resuspended in one fifth of the original volume and dialyzed against Buffer 'A' containing 50 mM NaCl. After dialysis the extract was centrifuged for 30 min at 25,000×g. Prior to affinity chromatography, Triton X-100™ (0.5%), KCl (0.3 M) and tRNA (50 g/ml) were added. Affinity oligonucleotide (5'-biotinTEG-biotinTEG-biotinTEG-GTA GAC CTG TTA CCA guu agg guu ag 3' [SEQ ID NO: 16]; lower case represents 2' O-methyl ribonucleotides and upper case represents deoxynucleotides) was added to the extract (1 nmol per 10 ml of extract). After an incubation of 10 min at 30° C., Neutravidin beads (Pierce; 250 µl of a 50% suspension) were added and the mixture was rotated overnight at 4° C. The beads were pelleted and washed three times with Buffer 'B' containing 0.3 M KCl, twice with Buffer 'B' containing 0.6 M KCl, and twice more with Buffer B containing 0.3 M KCl. Telomerase was eluted in Buffer 'B' containing 0.3 M KCl, 0.15% Triton X-100™ and a 2.5 molar excess of displacement oligonucleotide (5'-CTA ACC CTA ACT GGT AAC AGG TCT AC-3' [SEQ ID NO: 17] at 0.5 ml per 125 µl of packed Neutravidin beads) for 30 min. at room temperature. A second elution was performed and pooled with the first. Purified extracts typically had specific activities of 10 fmol nucleotides incorporated/min/µl extract, or 200 nucleotides/min/mg total protein.

| Buffer 'A' | Buffer 'B' |
|---|---|
| 20 mM Hepes pH 7.9 | 20 mM Hepes pH 7.9 |
| 1 mM MgCl2 | 1 mM EDTA |
| 1 mM DTT | 1 mM DTT |
| 1 mM EGTA | 10% glycerol |
| 10% glycerol | 0.5 Triton X-100 ™ |

EXAMPLE 7

Telomerase Inhibition by Oligonucleotide Conjugates

Bio-Tel FlashPlate Assay

A suitable assay for detection and/or measurement of telomerase activity is based on a measurement of the addition of TTAGGG (SEQ ID NO. 8) telomeric repeats to a biotinylated telomerase substrate primer, a reaction catalyzed by telomerase. The biotinylated products are captured in streptavidin-coated microtiter plates. An oligonucleotide probe complementary to 3.5 telomere repeats labeled with $^{33}$P is used for measuring telomerase products, as described below. Unbound probe is removed by washing and the amount of probe annealing to the captured telomerase products is determined by scintillation counting.

The data provided in Tables 1 and 2 below were obtained by performing the assay as described below:

1. Oligonucleotide conjugates were stored as concentrated stocks and dissolved in PBS.
2. For testing, the oligonucleotide conjugates were diluted to a 15× working stock in PBS and 2 µl was dispensed into two wells of a 96-well microtiter dish (assayed in duplicate).
3. Telomerase extract was diluted to a specific activity of 0.04-0.09 fmol dNTP incorporated/min./µl in Telomerase Dilution Buffer and 18 µl added to each sample well to preincubate with compound for 30 minutes at room temperature.
4. The telomerase reaction was initiated by addition of 10 µl Master Mix to the wells containing telomerase extract and oligonucleotide compound being tested. The plates were sealed and incubated at 37° C. for 90 min.
5. The reaction was stopped by the addition of 10 µl HCS.
6. 25 µl of the reaction mixture was transferred to a 96-well streptavidin-coated FlashPlate™ (NEN) and incubated for 2 hours at room temperature with mild agitation.
7. The wells were washed three times with 180 µl 2×SSC without any incubation.
8. The amount of probe annealed to biotinylated telomerase products was detected in a scintillation counter.

Buffers:
Telomerase Dilution Buffer
50 mM Tris-acetate, pH 8.2
1 mM DTT
1 mM EGTA
1 mM MgCl$_2$
830 nM BSA
Master Mix (MM)
50 mM Tris-acetate, pH 8.2
1 mM DTT
1 mM EGTA
1 mM MgCl$_2$
150 mM K acetate
10 µM dATP
20 µM dGTP
120 µM dTTP
100 nM biotinylated primer (5'-biotin-AATCCGTC-GAGCAGAGTT-3') [SEQ ID NO.: 18]
5.4 nM labeled probe [5'-CCCTAACCCTAAC-CCTAACCC-$^{33}$P) A$_{150}$-3'] [SEQ ID NO: 19]; specific activity approximately 10$^9$ cpm/µg or higher
Hybridization Capture Solution (HCS)
12×SSC (1×=150 mM NaCl/30 mM Na$_3$Citrate)
40 mM EDTA
40 mM Tris-HCl, pH 7.0

Using the foregoing assay, various oligonucleotide conjugates were tested, and the data is presented in Tables 1 and 2. As can be seen, the addition of the conjugated A group to the oligonucleotides typically enhanced the inhibitory activity of the oligonucleotide, sometimes by several orders of magnitude.

TABLE 1

Evaluation Of Oligonucleotide Conjugates As Telomerase Inhibitors

| | (IC$_{50}$ µM) | |
|---|---|---|
| Oligonucleotide Conjugate | NP | NPS |
| GGGTTAG (unconjugated) | 0.6 | 0.008 |
| GGGTTAG-L1-F | 0.08 | 0.002 |
| GGGTTAG-L2-F | 0.06 | 0.003 |

TABLE 1-continued

Evaluation Of Oligonucleotide Conjugates As Telomerase Inhibitors

| Oligonucleotide Conjugate | (IC$_{50}$ µM) | |
|---|---|---|
| | NP | NPS |
| GTTAGG (unconjugated) | 0.47 | 0.12 |
| GTTAGG-L1-F | 0.2 | 0.016 |
| GTTAGG-L2-F | 1.5 | 0.015 |
| TTAGGG (unconjugated) | 11.0 | 1.2 |
| TTAGGG-L1-F | 0.034 | 0.003 |
| TTAGGG-L2-F | 2.0 | 0.009 |
| F-L2-TTAGGG | | 0.007 |
| F-L2-TTAGGG-L1-F | | 0.005 |
| TTAGGG-L2-Tr | 11.5 | |
| TTAGGG-L1-Tr | 0.4 | 0.04 |
| TTAGGG-L1-X | 0.14 | 0.09 |
| A-L2-TTAGGG | 1.0 | 0.06 |
| A-L2-TTAGGG-L1-F | 0.022 | |
| AGGG (unconjugated) | 100, >1 | 0.087, 0.05, 0.03 |
| AGGG-L1-F | >1 | 0.018 |
| GGGTTAG (unconjugated) | 0.1, 1, 0.6* | 0.009, 0.005, 0.01 |
| GGGTTAG-L1-F | 0.1338, 0.0762, 0.196 | 0.002, 0.005, 0.005 |
| GGGTTAG-L2-F | 0.059 | 0.003, 0.005 |
| GGGTTAG-L1-Tr | 0.436, 0.933 | 0.029, 0.077 |
| TGAGT (unconjugated) | 0.399 | 0.036 |
| TGAGT-L1-F | 0.173, 0.272 | 0.010, 0.029 |
| GTAGGT | 0.098, 0.162 | 0.140, 0.117 |
| GTAGGT-L1-F | 0.0156, 0.032, 0.015 | 0.099, 0.035, 0.033 |

Key:
All conjugates shown in Table 1 were conjugated with a Type 1 or Type 2 linker to the 5' or 3' sugar ring of the oligonucleotide sequence, represented by the placement of the conjugated aromatic group to the left (5') or right (3') of the oligonucleotide sequence, respectively.
NP indicates that the oligonucleotide has N3' → P5' phosphoramidate internucleoside linkages
NPS indicates that the oligonucleotide has N3' → P5' thio-phosphoramidate internucleoside linkages
L1: Type 1 linker (thiourea)
L2: Type 2 linker (C5 or C6)
Conjugated aromatic groups shown:
F: fluorescein.
Tr: N,N'-tetramethylrhodamine
A: Acridine

TABLE 2

Evaluation Of Oligonueleotide Conjugates As Telomerase Inhibitors

| Oligonucleotide Conjugate | (IC$_{50}$ µM) | |
|---|---|---|
| | NP | NPS |
| GGGTTAG (unconjugated) | 0.1, 1, 0.6, 0.081 | 0.009, 0.005, 0.010 |
| GGGTTA-ORS1-G* | 0.477, 0.626 | 0.026, 0.031 |
| GGGTTA-ORS2-G* | 0.005, 0.010 | |
| TTAGGG (unconjugated) | 0.039, 0.079, >1 | 1.17, 1-55 |
| TTAGG-ORS1-G* | >1, 0.691 | 0.305, 0.4 |
| TTAGGG-ORS1-G* | >1 | 0.0858, 0.108 |

TABLE 2-continued

Evaluation Of Oligonueleotide Conjugates As Telomerase Inhibitors

| Oligonucleotide Conjugate | ($IC_{50}$ µM) | |
|---|---|---|
| | NP | NPS |
| TTAGG-ORS2-G* | 0.004, 0.005, 0.310, 0.115, 0.721, >1, 5.15 | 0.102, 0.24 |
| TAA-ORS2-G*G*G* | 0.004, 0.009 | 0.102, 0.088 |

Key:
All conjugates shown in Table 2 were conjugated with a Type 3 linker (ORS1 or ORS2) to the 3' sugar ring of the oligonucleotide sequence, represented by the placement of the conjugated aromatic group to the right (3') of the oligonucleotide sequence.
NP indicates that the oligonucleotide has N3' → P5' phosphoramidate internucleoside linkages.
NPS indicates that the oligonucleotide has N3' → P5' thio-phosphoramidate internucleoside linkages,
G* is the conjugated aromatic group guanine,
ORS1 and ORS2 are Open Ring Sugar Linkers 1 and 2, respectively.
TAA-ORS2-G*G*G* is a conjugated oligonucleotide in which a first guanine nucleobase is conjugated to the 3' sugar of the oligoucleotide sequence TAA through an ORS2 linker, and two additional guanine nucleobases are conjugated sequentially to the first guanine nueleobase through ORS2 open ring sugar linkers.

EXAMPLE 8

Anti-Tumor Activity of Oligonucleotide Conjugates

Cell Assays a. Inhibition of Telomerase Activity in Cells and Inhibition of Tumor Cell Growth The following is a description of a general cell assay method that may be used to determine the effect of the test conjugates on tumor cell growth. Colonies of human breast epithelial cells (spontaneously immortalized) are prepared using standard methods and materials. Colonies are prepared by seeding 15-centimeter dishes with about $10^6$ cells in each dish. The dishes are incubated to allow the cell colonies to grow to about 80% confluence, at which time each of the colonies are divided into two groups. One group was exposed to a subacute dose of thio-phosphoramidate polynucleotide conjugate of experiment 9 at a predetermined concentration (e.g., between about 100 nM and about 20 µM) for a period of about 4-8 hours after plating following the split. The second group of cells are similarly exposed to an unconjugated control oligonucleotide.

Each group of cells is then allowed to continue to divide, and the groups are split evenly again (near confluence). The same number of cells are e seeded for continued growth. The test thio-phosphoramidate oligonucleotide conjugate or control oligonucleotide is added every fourth day to the samples at the same concentration delivered initially. In certain experiments, the cells may also be treated with an oligonucleotide uptake enhancer, such as FuGENE6™ (Roche). Reduction of telomerase activity associated with the oligonucleotide treatment is determined by TRAP assay.

In addition, telomere lengths in the treated cells may be determined by digesting the DNA of the cell samples using restriction enzymes specific for sequences other than the repetitive $T_2AG_3$ sequence of human telomeres (TRF analysis). The digested DNA is separated by size using standard techniques of gel electrophoresis to determine the lengths of the telomeric repeats, which appear, after probing with a telomere DNA probe, on the gel as a smear of high-molecular weight DNA (approximately 2 Kb-15 Kb).

These approaches were used to determine the effect of treatment with the conjugate TTAGGG-L1-F on HME50 and Caki-1 cells. $IC_{50}$ values in the range of ca. 5 µmole (in the range of 1-20 µmole) were obtained in the absence of an uptake enhancer. When cells were incubated with this conjugate in the presence of FuGENE6 they underwent cell crisis and apoptosis after approximately 15 days of treatment. Growth of control cells was not affected.

b. Specificity

The short oligonucleotide conjugates of the invention are screened for activity ($IC_{50}$) against telomerase and other enzymes known to have RNA components by performing hybridization tests or enzyme inhibition assays using standard techniques. Oligonucleotides having lower $IC_{50}$ values for telomerase as compared to the $IC_{50}$ values toward the other enzymes being screened are said to possess specificity for telomerase.

c. Cytotoxicity

The cell death (XTT) assay for cytotoxicity are performed using HME50-5E, Caki-1, A431, ACHN, and A549 cell types. The cell lines used in the assay are exposed to one of the short oligonucleotide conjugates for 72 hours at concentrations ranging from about 1 µM to about 100 µM in the presence and absence of lipids. During this period, the optical density (OD) of the samples is determined for light at 540 nanometers (nm). The $IC_{50}$ values obtained for the various cell types are generally less than 1 µM. Thus, no significant cytotoxic effects are expected to be observed at concentrations less than about 100 µM. It will be appreciated that other tumor cells lines such as the ovarian tumor cell lines OVCAR-5 and SK-OV-3 can be used to determine cytotoxicity in addition to control cell lines such as normal human BJ cells. Other assays for cytotoxicity such as the MTT assay (see Berridge et al., Biochemica 4:14-19, 1996) and the alamarBluer™ assay (U.S. Pat. No. 5,501,959) can be used as well.

Preferably, to observe any telomerase inhibiting effects the oligonucleotide conjugates should be administered at a concentration below the level of cytotoxicity. Nevertheless, since the effectiveness of many cancer chemotherapeutics derives from their cytotoxic effects, it is within the scope of the present invention that the oligonucleotide conjugates of the present invention be administered at any dose for which chemotherapeutic effects are observed.

In Vivo Animal Studies

A human tumor xenograft model in which OVCAR-5 tumor cells are grafted into nude mice can be constructed using standard techniques and materials. The mice are divided into two groups. One group is treated intraperitoneally with a short oligonucleotide conjugates of the invention. The other group is treated with a control comprising a mixture of phosphate buffer solution (PBS) and an oligonucleotide complementary with telomerase RNA but has at least a one base mismatch with the sequence of telomerase RNA. The average tumor mass for mice in each group is determined periodically following the xenograft using standard methods and materials.

In the group treated with oligonucleotide conjugates of the invention, the average tumor mass is expected to increase following the initial treatment for a period of time, after which time the tumor mass is expected to stabilize and then begin to decline. Tumor masses in the control group are expected to increase throughout the study. Thus, the oligonucleotide conjugates of the invention are expected to lessen dramatically the rate of tumor growth and ultimately induce reduction in tumor size and elimination of the tumor.

Thus, the present invention provides novel oligonucleotide conjugates and methods for inhibiting telomerase activity and treating disease states in which telomerase activity has deleterious effects, especially cancer. The oligonucleotide conjugates of the invention provide a highly selective and effective treatment for malignant cells that require telomerase activity to remain immortal; yet, without affecting non-malignant cells.

While the preferred embodiment of the invention has been illustrated and described, it will be appreciated that various changes can be made therein without departing from the spirit and scope of the invention.

---

We claim:

1. A method for inhibiting a tumor cell comprising contacting a tumor cell that expresses telomerase with a conjugated oligonucleotide selected from the group consisting of:

GGGTTAG-L1-F;

GGGTTAG-L2-F;

GGCTTAG-L1-Tr;

GTTAGG-L1-F;

GTTAGG-L2-F;

TTAGGG-L1-F;

TTAGGG-L2-F;

F-L2-TTAGGG;

F-L2-TTAGGG-L1-F;

TTAGGG-L1-Tr;

Acridine-L2-TTAGGG;

Acridine-L2-TTAGGG-L1-F;

AGGG-L1-F;

TGAGT-L1-F;
and

GTAGGT-L1-F;

wherein:
the conjugated oligonucleotide is joined by N3'→P5' phosphoramidate or N3'→P5' thiophosphoramidate intersubunit linkages;
L1 is a thiourea linker;
L2 is a C5 or C6 linker;
F is fluorescein, and
Tr is N,N'-tetramethylrhodamine.

2. The method of claim 1, wherein the conjugated oligonucleotide is joined by N3'→P5' phosphoramidate intersubunit linkages.

3. The method of claim 1, wherein the conjugated oligonucleotide is joined by N3'→P5' thiophosphoramidate intersubunit linkages.

4. The method of claim 3, wherein the conjugated oligonucleotide is TTAGGG-L1-F.

* * * * *